(12) United States Patent
Meyer et al.

(10) Patent No.: US 9,032,953 B2
(45) Date of Patent: May 19, 2015

(54) MODULAR AEROSOL DELIVERY SYSTEM

(75) Inventors: Adam Meyer, London (CA); James Schmidt, London (CA); Chris Dobson, Sebringville (CA); Daniel Engelbreth, London (CA)

(73) Assignee: Trudell Medical International, London (CA)

( * ) Notice: Subject to any disclaimer, the term of this patent is extended or adjusted under 35 U.S.C. 154(b) by 0 days.

(21) Appl. No.: 13/397,284

(22) Filed: Feb. 15, 2012

(65) Prior Publication Data
US 2012/0145148 A1 Jun. 14, 2012

Related U.S. Application Data

(63) Continuation of application No. 12/603,700, filed on Oct. 22, 2009.

(60) Provisional application No. 61/107,435, filed on Oct. 22, 2008.

(51) Int. Cl.
*A61M 16/14* (2006.01)
*A61M 15/00* (2006.01)
(Continued)

(52) U.S. Cl.
CPC ....... *A61M 15/0086* (2013.01); *A61M 15/0065* (2013.01); *A61M 15/009* (2013.01);
(Continued)

(58) Field of Classification Search
CPC . A61M 11/00; A61M 15/00; A61M 15/0065; A61M 16/00; A61M 2011/00; A61M 2015/00; A61M 2015/0065; A61M 15/0068; A61M 15/007; A61M 15/0071; A61M 15/0086
USPC ............ 128/200.11, 200.14, 200.23, 200.24, 128/203.12, 203.15, 203.16, 204.18, 128/205.23, 203.28; 222/23, 24, 29, 30, 44, 222/635
See application file for complete search history.

(56) References Cited

U.S. PATENT DOCUMENTS 165,054 A 6/1875 Baldwin
498,851 A 6/1893 Jones
(Continued)

FOREIGN PATENT DOCUMENTS

AU 598250 B2 6/1990
CA 535 518 A 1/1957
(Continued)

OTHER PUBLICATIONS

U.S. Department of Health and Human Services, Food and Drug Administration, Center for Drug Evaluation and Research (CDER)—Clinical, "Guidance for Industry: Integration of Dose-Counting Mechanisms into MDI Drug Products—Draft Guidance," dated Nov. 2001, 6 pages.
Translation of Japanese Office Action from Japanese Application No. 2008-019458, dated Sep. 29, 2009, 2 pages.
(Continued)

*Primary Examiner* — Valerie L Skorupa
(74) *Attorney, Agent, or Firm* — Brinks Gilson & Lione

(57) ABSTRACT

An adapter for use in a breathing circuit including a housing with a conduit having a ventilator port adapted to be coupled to a breathing circuit and a patient port adapted to communicate with a patient interface. A medicament container receptacle communicates with the conduit between the ventilator port and the patient port. The receptacle includes a support block having a well shaped to receive a valve stem extending from a container of medicament and an actuator finger extending upwardly in the receptacle adjacent the support block. The actuator finger is adapted to actuate a dose counter coupled to the container.

20 Claims, 12 Drawing Sheets

(51) Int. Cl.
*A61M 11/00* (2006.01)
*A61M 11/04* (2006.01)
*A61M 16/00* (2006.01)

(52) U.S. Cl.
CPC ........ *A61M15/0068* (2014.02); *A61M 15/0088* (2014.02); *A61M 11/04* (2013.01); *A61M 16/0078* (2013.01)

(56) References Cited

U.S. PATENT DOCUMENTS

| | | |
|---|---|---|
| 1,219,858 A | 3/1917 | Patterson |
| 2,455,962 A | 12/1948 | Wheeler et al. |
| 2,580,292 A | 12/1951 | Geary et al. |
| 2,587,147 A | 2/1952 | Guion et al. |
| 2,630,027 A | 3/1953 | Wunderlich |
| 2,644,452 A | 7/1953 | Brown |
| 2,767,680 A | 10/1956 | Lermer |
| 2,770,711 A | 11/1956 | Baranowski |
| 2,883,086 A | 4/1959 | Davison et al. |
| 2,939,597 A | 6/1960 | Greene |
| 2,943,730 A | 7/1960 | Tregilgas |
| 2,953,242 A | 9/1960 | Shaw |
| 3,001,524 A | 9/1961 | Maison et al. |
| 3,073,468 A | 1/1963 | Arneson |
| 3,085,745 A | 4/1963 | Auberger |
| 3,119,557 A | 1/1964 | Chapman |
| 3,120,318 A | 2/1964 | Rigor |
| 3,148,801 A | 9/1964 | Radeloff et al. |
| 3,151,599 A | 10/1964 | Livingston |
| 3,170,597 A | 2/1965 | Reichenberger |
| 3,187,963 A | 6/1965 | Anderson |
| 3,189,232 A | 6/1965 | Joffe |
| 3,191,867 A | 6/1965 | Helms |
| 3,240,389 A | 3/1966 | Genua |
| 3,334,731 A | 8/1967 | Dale |
| 3,344,951 A | 10/1967 | Gervais |
| 3,361,306 A | 1/1968 | Grim |
| 3,402,863 A | 9/1968 | Green |
| 3,419,187 A | 12/1968 | Bazarnic |
| 3,446,179 A | 5/1969 | Bender |
| 3,477,561 A | 11/1969 | Espinal |
| 3,495,567 A | 2/1970 | Hayes et al. |
| 3,511,409 A | 5/1970 | Huck |
| 3,549,057 A | 12/1970 | Perez |
| 3,568,629 A | 3/1971 | Porter |
| 3,572,282 A | 3/1971 | Trump et al. |
| 3,589,563 A | 6/1971 | Carragan et al. |
| 3,612,349 A | 10/1971 | Thomas |
| 3,654,890 A | 4/1972 | Rigney et al. |
| 3,655,952 A | 4/1972 | Johnson et al. |
| 3,688,945 A | 9/1972 | Harman, Jr. et al. |
| 3,753,417 A | 8/1973 | Garby |
| 3,766,882 A | 10/1973 | Babbitt, III |
| 3,789,843 A | 2/1974 | Armstrong et al. |
| 3,792,242 A | 2/1974 | Hanson |
| 3,796,348 A | 3/1974 | Zipper |
| 3,797,748 A | 3/1974 | Nozawa et al. |
| 3,802,608 A | 4/1974 | Gullett |
| 3,831,808 A | 8/1974 | Bender |
| 3,831,812 A | 8/1974 | Dolan |
| 3,845,883 A | 11/1974 | Johnson et al. |
| 3,848,774 A | 11/1974 | Schimke |
| 3,886,879 A | 6/1975 | Frost et al. |
| 3,887,099 A | 6/1975 | Gillman et al. |
| 3,921,568 A | 11/1975 | Fish |
| 3,926,326 A | 12/1975 | Grau |
| 3,950,939 A | 4/1976 | Meisner |
| 3,960,713 A | 6/1976 | Carey |
| 3,977,554 A | 8/1976 | Costa |
| 3,994,421 A | 11/1976 | Hansen |
| 4,011,829 A | 3/1977 | Wachsmann et al. |
| 4,029,033 A | 6/1977 | Kerwin et al. |
| 4,034,757 A | 7/1977 | Glover |
| 4,037,719 A | 7/1977 | Perlmutter |
| 4,069,935 A | 1/1978 | Hampel |
| 4,069,942 A | 1/1978 | Marshall et al. |
| 4,074,831 A | 2/1978 | Roach |
| 4,078,661 A | 3/1978 | Thomas |
| 4,094,408 A | 6/1978 | Ford |
| 4,117,952 A | 10/1978 | Grimes |
| 4,162,746 A | 7/1979 | Anderson et al. |
| 4,164,301 A | 8/1979 | Thayer |
| 4,171,753 A | 10/1979 | Vreede |
| 4,188,984 A | 2/1980 | Lyall |
| 4,220,247 A | 9/1980 | Kramer |
| 4,291,688 A | 9/1981 | Kistler |
| 4,300,548 A | 11/1981 | Jones |
| 4,319,128 A | 3/1982 | Dow, Jr. et al. |
| 4,345,541 A | 8/1982 | Villa-Real |
| 4,347,804 A | 9/1982 | Villa-Real |
| 4,347,853 A | 9/1982 | Gereg et al. |
| 4,350,265 A | 9/1982 | Griffiths et al. |
| 4,354,621 A | 10/1982 | Knickerbocker |
| 4,357,192 A | 11/1982 | Moser |
| 4,365,722 A | 12/1982 | Kramer |
| 4,368,381 A | 1/1983 | Ishiyama |
| 4,405,045 A | 9/1983 | Villa-Real |
| 4,419,016 A | 12/1983 | Zoltan |
| 4,432,300 A | 2/1984 | Lyss |
| 4,436,223 A | 3/1984 | Wilson |
| 4,440,306 A | 4/1984 | Van Buskirk et al. |
| 4,489,834 A | 12/1984 | Thackrey |
| 4,500,005 A | 2/1985 | Forrester |
| 4,501,370 A | 2/1985 | Kelley |
| 4,511,150 A | 4/1985 | Seguenot |
| 4,523,933 A | 6/1985 | Laush et al. |
| 4,528,933 A | 7/1985 | Allen |
| 4,534,345 A | 8/1985 | Wetterlin |
| 4,538,744 A | 9/1985 | Weissenborn |
| 4,548,157 A | 10/1985 | Hevoyan |
| 4,562,933 A | 1/1986 | Dennis |
| 4,565,302 A | 1/1986 | Pfeiffer et al. |
| 4,599,508 A | 7/1986 | Smetaniuk |
| 4,627,432 A | 12/1986 | Newell et al. |
| 4,634,012 A | 1/1987 | Kelley |
| 4,637,528 A | 1/1987 | Wachinski et al. |
| 4,641,759 A | 2/1987 | Kelley |
| 4,646,936 A | 3/1987 | Frazier et al. |
| 4,662,520 A | 5/1987 | Griffin |
| 4,664,107 A | 5/1987 | Wass |
| 4,666,051 A | 5/1987 | Trick |
| 4,668,218 A | 5/1987 | Virtanen |
| 2,841,190 A | 7/1987 | Sheck |
| 4,677,975 A | 7/1987 | Edgar et al. |
| 4,693,399 A | 9/1987 | Hickman et al. |
| 4,705,182 A | 11/1987 | Newell-Lewis |
| 4,722,729 A | 2/1988 | Dettbarn et al. |
| 4,723,673 A | 2/1988 | Tartaglia et al. |
| 4,727,886 A | 3/1988 | Conrardy et al. |
| 4,736,871 A | 4/1988 | Luciani et al. |
| 4,749,093 A | 6/1988 | Trick |
| 4,753,189 A | 6/1988 | Mastman et al. |
| 4,756,423 A | 7/1988 | Holtsch |
| 4,782,966 A | 11/1988 | Thackrey |
| 4,792,664 A | 12/1988 | Schwab |
| 4,817,822 A * | 4/1989 | Rand et al. .................. 222/38 |
| 4,890,572 A | 1/1990 | Huang |
| 4,934,358 A | 6/1990 | Nilsson et al. |
| 4,934,568 A | 6/1990 | Fuchs |
| 4,938,210 A | 7/1990 | Shene |
| 4,947,875 A | 8/1990 | Brooks et al. |
| 4,955,371 A | 9/1990 | Zamba et al. |
| 4,969,578 A | 11/1990 | Gander et al. |
| 4,973,250 A | 11/1990 | Milman |
| 4,984,158 A | 1/1991 | Hillsman |
| 5,009,338 A | 4/1991 | Barker |
| 5,011,032 A | 4/1991 | Rollman |
| 5,020,527 A | 6/1991 | Dessertine |
| 5,027,806 A | 7/1991 | Zoltan et al. |
| 5,027,808 A | 7/1991 | Rich et al. |
| 5,038,972 A | 8/1991 | Muderlak et al. |
| 5,056,454 A | 10/1991 | Turner |
| 5,060,643 A | 10/1991 | Rich et al. |

(56) References Cited

U.S. PATENT DOCUMENTS

| | | | |
|---|---|---|---|
| 5,069,204 A | 12/1991 | Smith et al. | |
| 5,082,129 A | 1/1992 | Kramer | |
| 5,082,130 A | 1/1992 | Weinstein | |
| 5,115,929 A | 5/1992 | Buono | |
| 5,174,473 A | 12/1992 | Marelli | |
| 5,184,761 A | 2/1993 | Lee | |
| 5,188,251 A | 2/1993 | Kusz | |
| 5,190,643 A | 3/1993 | Duncan et al. | |
| 5,209,375 A | 5/1993 | Fuchs | |
| 5,215,079 A | 6/1993 | Fine et al. | |
| 5,217,004 A | 6/1993 | Blasnik et al. | |
| 5,224,474 A | 7/1993 | Bloomfield | |
| 5,226,539 A | 7/1993 | Cheng | |
| 5,227,764 A | 7/1993 | Umemoto | |
| 5,228,586 A | 7/1993 | Fuchs | |
| 5,242,067 A | 9/1993 | Garby et al. | |
| 5,243,970 A | 9/1993 | Ambrosio et al. | |
| 5,261,548 A | 11/1993 | Barker et al. | |
| 5,263,475 A | 11/1993 | Altermatt et al. | |
| 5,284,133 A | 2/1994 | Burns et al. | |
| 5,289,946 A | 3/1994 | Fuchs | |
| 5,297,543 A | 3/1994 | Larson et al. | |
| 5,299,701 A | 4/1994 | Barker et al. | |
| 5,300,042 A | 4/1994 | Kossoff et al. | |
| 5,301,873 A | 4/1994 | Burke et al. | |
| 5,318,016 A | 6/1994 | Mecikalski | |
| 5,328,597 A | 7/1994 | Boldt, Jr. et al. | |
| 5,331,953 A | 7/1994 | Andersson et al. | |
| 5,335,823 A | 8/1994 | Fuchs et al. | |
| 5,349,944 A | 9/1994 | Chippendale et al. | |
| 5,349,945 A * | 9/1994 | Wass et al. | 128/200.23 |
| 5,356,012 A | 10/1994 | Tang et al. | |
| 5,356,406 A | 10/1994 | Schraga | |
| 5,357,946 A | 10/1994 | Kee et al. | |
| 5,363,842 A | 11/1994 | Mishelevich et al. | |
| 5,370,267 A | 12/1994 | Schroeder | |
| 5,378,233 A | 1/1995 | Haber et al. | |
| 5,379,804 A | 1/1995 | Dunn et al. | |
| 5,382,243 A | 1/1995 | Mulholland | |
| RE34,847 E | 2/1995 | Muderlak et al. | |
| 5,388,572 A | 2/1995 | Mulhauser et al. | |
| 5,392,768 A | 2/1995 | Johansson et al. | |
| 5,394,866 A | 3/1995 | Ritson et al. | |
| 5,397,028 A | 3/1995 | Jesadanont | |
| 5,411,173 A | 5/1995 | Weinstein | |
| 5,421,482 A | 6/1995 | Garby et al. | |
| 5,437,270 A | 8/1995 | Braithwaite | |
| 5,447,150 A | 9/1995 | Bacon | |
| 5,448,042 A | 9/1995 | Robinson et al. | |
| 5,468,233 A | 11/1995 | Schraga | |
| 5,474,058 A * | 12/1995 | Lix | 128/200.18 |
| 5,482,030 A * | 1/1996 | Klein | 128/200.23 |
| 5,482,163 A | 1/1996 | Hoffman | |
| 5,498,243 A | 3/1996 | Vallelunga et al. | |
| 5,505,192 A | 4/1996 | Samiotes et al. | |
| 5,505,195 A | 4/1996 | Wolf et al. | |
| 5,509,905 A | 4/1996 | Michel | |
| 5,519,197 A | 5/1996 | Robinson et al. | |
| 5,520,166 A | 5/1996 | Ritson et al. | |
| 5,522,378 A | 6/1996 | Ritson et al. | |
| 5,524,613 A | 6/1996 | Haber et al. | |
| 5,544,647 A | 8/1996 | Jewett et al. | |
| 5,549,101 A | 8/1996 | Trofast et al. | |
| 5,564,414 A | 10/1996 | Walker et al. | |
| 5,574,268 A | 11/1996 | Herman et al. | |
| 5,577,335 A | 11/1996 | Tucker | |
| 5,584,815 A | 12/1996 | Pawelka et al. | |
| 5,611,444 A | 3/1997 | Garby et al. | |
| 5,617,844 A * | 4/1997 | King | 128/200.18 |
| 5,622,163 A | 4/1997 | Jewett et al. | |
| 5,625,334 A | 4/1997 | Compton | |
| 5,625,659 A | 4/1997 | Sears | |
| 5,626,566 A | 5/1997 | Petersen et al. | |
| 5,638,970 A | 6/1997 | Garby et al. | |
| 5,657,748 A | 8/1997 | Braithwaite | |
| 5,676,129 A | 10/1997 | Rocci, Jr. et al. | |
| 5,687,710 A | 11/1997 | Ambrosio et al. | |
| 5,692,492 A | 12/1997 | Bruna et al. | |
| 5,694,882 A | 12/1997 | Marshall | |
| 5,697,916 A | 12/1997 | Schraga | |
| 5,701,886 A | 12/1997 | Ryatt | |
| 5,718,355 A | 2/1998 | Garby et al. | |
| 5,724,957 A | 3/1998 | Rubsamen et al. | |
| 5,732,836 A | 3/1998 | Barker et al. | |
| 5,740,792 A | 4/1998 | Ashley et al. | |
| 5,758,638 A | 6/1998 | Kreamer | |
| 5,772,074 A | 6/1998 | Dial et al. | |
| 5,794,612 A | 8/1998 | Wachter et al. | |
| 5,799,651 A | 9/1998 | Garby et al. | |
| 5,803,283 A | 9/1998 | Barker et al. | |
| 5,809,996 A | 9/1998 | Alldredge | |
| 5,809,997 A | 9/1998 | Wolf | |
| 5,826,571 A | 10/1998 | Casper et al. | |
| 5,829,434 A | 11/1998 | Ambrosio et al. | |
| 5,845,777 A | 12/1998 | Najmi | |
| 5,852,590 A | 12/1998 | De La Huerga | |
| 5,871,007 A | 2/1999 | Clark, Jr. | |
| 5,873,995 A | 2/1999 | Huang et al. | |
| 5,882,507 A | 3/1999 | Tanner et al. | |
| 5,896,855 A | 4/1999 | Hobbs | |
| 5,896,990 A | 4/1999 | Barzana | |
| 5,899,201 A | 5/1999 | Schultz et al. | |
| 5,904,139 A | 5/1999 | Hauser | |
| 5,957,896 A | 9/1999 | Bendek et al. | |
| 5,961,495 A | 10/1999 | Walters et al. | |
| 5,988,496 A | 11/1999 | Bruna | |
| 6,000,159 A | 12/1999 | Hornung | |
| 6,001,082 A | 12/1999 | Dair et al. | |
| 6,012,450 A | 1/2000 | Rubsamen | |
| 6,014,972 A * | 1/2000 | Sladek | 128/203.12 |
| 6,029,659 A | 2/2000 | O'Connor | |
| 6,059,133 A | 5/2000 | Lai | |
| 6,062,214 A | 5/2000 | Howlett | |
| 6,076,521 A | 6/2000 | Lindahl et al. | |
| 6,082,358 A | 7/2000 | Scarrott et al. | |
| 6,089,180 A | 7/2000 | Nichols, Jr. | |
| 6,096,010 A | 8/2000 | Walters et al. | |
| 6,119,684 A | 9/2000 | Nohl et al. | |
| 6,138,669 A | 10/2000 | Rocci, Jr. et al. | |
| 6,142,339 A * | 11/2000 | Blacker et al. | 222/23 |
| 6,148,815 A | 11/2000 | Wolf | |
| 6,149,054 A | 11/2000 | Cirrillo | |
| 6,155,251 A | 12/2000 | Hauser | |
| 6,161,724 A | 12/2000 | Blacker et al. | |
| 6,164,494 A | 12/2000 | Marelli | |
| 6,182,655 B1 | 2/2001 | Keller et al. | |
| 6,186,364 B1 | 2/2001 | Dobbs | |
| 6,202,642 B1 | 3/2001 | McKinnon et al. | |
| 6,221,053 B1 | 4/2001 | Walters et al. | |
| 6,223,744 B1 | 5/2001 | Garon | |
| 6,234,168 B1 | 5/2001 | Bruna | |
| 6,283,365 B1 | 9/2001 | Bason | |
| 6,318,600 B1 | 11/2001 | Winnett et al. | |
| 6,328,037 B1 | 12/2001 | Scarrott et al. | |
| 6,336,453 B1 | 1/2002 | Scarrott et al. | |
| 6,360,739 B1 | 3/2002 | Rand et al. | |
| 6,405,727 B1 | 6/2002 | MacMichael et al. | |
| 6,415,785 B1 | 7/2002 | Stage | |
| 6,425,392 B1 | 7/2002 | Sosiak | |
| 6,431,168 B1 | 8/2002 | Rand et al. | |
| 6,435,372 B1 | 8/2002 | Blacker et al. | |
| 6,446,627 B1 | 9/2002 | Bowman et al. | |
| 6,463,929 B1 | 10/2002 | Scheuch et al. | |
| 6,474,331 B1 | 11/2002 | Rand et al. | |
| 6,481,438 B1 | 11/2002 | Gallem et al. | |
| 6,484,717 B1 | 11/2002 | Dagsland et al. | |
| 6,516,799 B1 | 2/2003 | Greenwood et al. | |
| 6,529,446 B1 | 3/2003 | De La Huerga | |
| 6,561,384 B2 | 5/2003 | Blacker et al. | |
| 6,601,582 B2 | 8/2003 | Rand et al. | |
| 6,615,827 B2 | 9/2003 | Greenwood et al. | |
| 6,659,307 B1 | 12/2003 | Stradella | |
| 6,679,251 B1 | 1/2004 | Gallem et al. | |
| 6,701,917 B2 | 3/2004 | O'Leary | |

(56) References Cited

U.S. PATENT DOCUMENTS

| | | | |
|---|---|---|---|
| 6,718,972 | B2 | 4/2004 | O'Leary |
| 6,729,330 | B2 | 5/2004 | Scarrott et al. |
| 6,752,153 | B1 | 6/2004 | Eckert |
| 6,761,161 | B2 | 7/2004 | Scarrott et al. |
| 6,766,799 | B2 | 7/2004 | Edwards et al. |
| 6,769,601 | B2 | 8/2004 | Haikarainen et al. |
| 6,907,876 | B1 | 6/2005 | Clark et al. |
| 6,938,796 | B2 | 9/2005 | Blacker et al. |
| 6,997,349 | B2 | 2/2006 | Blacker et al. |
| 7,137,391 | B2 | 11/2006 | Bruna |
| 7,143,764 | B1 | 12/2006 | Dagsland et al. |
| 7,143,908 | B2 | 12/2006 | Blacker et al. |
| 7,156,258 | B2 | 1/2007 | Eckert |
| 7,360,537 | B2 | 4/2008 | Snyder et al. |
| 7,407,066 | B2 | 8/2008 | Ouyang et al. |
| 7,555,995 | B1 | 7/2009 | Stump et al. |
| 7,575,130 | B2 | 8/2009 | Blacker et al. |
| 7,661,423 | B2 * | 2/2010 | Brand et al. ............ 128/200.23 |
| 7,793,798 | B2 | 9/2010 | Stradella et al. |
| 7,984,826 | B2 | 7/2011 | Blacker et al. |
| 2002/0000225 | A1 | 1/2002 | Schuler et al. |
| 2002/0069870 | A1 * | 6/2002 | Farmer .................... 128/200.22 |
| 2002/0104531 | A1 * | 8/2002 | Malone ................... 128/200.23 |
| 2002/0153005 | A1 | 10/2002 | Scarrott et al. |
| 2003/0183225 | A1 | 10/2003 | Knudsen |
| 2003/0200964 | A1 | 10/2003 | Blakley et al. |
| 2003/0205227 | A1 | 11/2003 | Hodson |
| 2003/0209239 | A1 * | 11/2003 | Rand et al. ............... 128/200.23 |
| 2004/0065326 | A1 | 4/2004 | MacMichael et al. |
| 2004/0069301 | A1 | 4/2004 | Bacon |
| 2004/0089296 | A1 | 5/2004 | Bowden |
| 2004/0094147 | A1 | 5/2004 | Schyra et al. |
| 2004/0144798 | A1 | 7/2004 | Ouyang et al. |
| 2004/0149772 | A1 | 8/2004 | Ouyang |
| 2004/0149773 | A1 | 8/2004 | Ouyang et al. |
| 2004/0221840 | A1 | 11/2004 | Stockman-Lamb |
| 2004/0255935 | A1 | 12/2004 | Bruna |
| 2004/0255936 | A1 | 12/2004 | Urbanus |
| 2005/0011515 | A1 | 1/2005 | Lee et al. |
| 2005/0039746 | A1 * | 2/2005 | Grychowski et al. .... 128/204.18 |
| 2005/0056276 | A1 | 3/2005 | Schuler et al. |
| 2005/0217667 | A1 * | 10/2005 | Dhuper et al. ........... 128/200.23 |
| 2005/0268905 | A1 | 12/2005 | Rasmussen et al. |
| 2005/0284471 | A1 | 12/2005 | Bruna |
| 2006/0060192 | A1 | 3/2006 | Lu et al. |
| 2006/0096594 | A1 * | 5/2006 | Bonney et al. ........... 128/202.17 |
| 2006/0254579 | A1 * | 11/2006 | Grychowski et al. .... 128/200.22 |
| 2006/0254581 | A1 | 11/2006 | Genova et al. |
| 2006/0260608 | A1 | 11/2006 | Armstrong et al. |
| 2007/0056581 | A1 | 3/2007 | Obuz |
| 2007/0074718 | A1 | 4/2007 | Austin |
| 2007/0084462 | A1 | 4/2007 | Allen |
| 2007/0277817 | A1 * | 12/2007 | Innocenzi ................ 128/200.23 |
| 2008/0066741 | A1 | 3/2008 | LeMahieu et al. |
| 2008/0264412 | A1 | 10/2008 | Meyer et al. |
| 2010/0139653 | A1 * | 6/2010 | Schloss ................... 128/203.12 |

FOREIGN PATENT DOCUMENTS

| | | |
|---|---|---|
| CA | 2 152 088 A | 7/1994 |
| CA | 2 181 789 C | 6/1996 |
| CA | 2 486 892 A1 | 12/1998 |
| CA | 2 315 777 A1 | 7/1999 |
| CA | 2 331 179 A1 | 11/1999 |
| CA | 2 383 425 A1 | 3/2001 |
| CA | 2 388 958 A1 | 3/2001 |
| CA | 2 414 118 A1 | 1/2002 |
| CA | 2 420 171 A1 | 3/2002 |
| DE | 6 603 758 U | 7/1969 |
| DE | 27 02 539 A1 | 1/1977 |
| DE | 33 36 486 A1 | 4/1984 |
| DE | 86 02 238 U1 | 4/1986 |
| DE | 85 90 143 U1 | 4/1987 |
| EP | 0 028 929 A2 | 5/1981 |
| EP | 0 098 939 A2 | 1/1984 |
| EP | 0 114 617 A2 | 8/1984 |
| EP | 0 063 599 B1 | 6/1986 |
| EP | 0 230 323 B1 | 7/1987 |
| EP | 0 236 871 A2 | 9/1987 |
| EP | 0 269 496 A2 | 6/1988 |
| EP | 0 280 104 B1 | 8/1988 |
| EP | 0 488 609 A1 | 6/1992 |
| EP | 0 559 757 B1 | 9/1993 |
| EP | 0 949 584 A2 | 10/1999 |
| EP | 1 036 569 A2 | 9/2000 |
| EP | 1 369 139 A1 | 12/2003 |
| EP | 1 220 802 B1 | 2/2004 |
| FR | 2 743 055 A1 | 7/1997 |
| GB | 998 148 A | 7/1965 |
| GB | 1 058 636 A | 2/1967 |
| GB | 1 290 484 A | 9/1972 |
| GB | 1 317 315 A | 5/1973 |
| GB | 2 036 695 A | 7/1980 |
| GB | 2 063 075 A | 6/1981 |
| GB | 2 092 991 A | 8/1982 |
| GB | 2 104 393 A | 3/1983 |
| GB | 2 191 032 A | 12/1987 |
| GB | 2 195 544 A | 4/1988 |
| GB | 2 267 936 A | 12/1993 |
| GB | 2 301 040 A | 11/1996 |
| GB | 2 348 928 A | 10/2000 |
| GB | 2 414 187 A | 11/2005 |
| JP | 61-55759 U | 4/1986 |
| JP | 62-121670 U | 8/1987 |
| JP | 04-050059 U | 4/1992 |
| JP | 06-26891 A | 4/1994 |
| WO | WO 86/02275 A1 | 4/1986 |
| WO | WO 87/04354 A1 | 8/1987 |
| WO | WO 90/10470 A1 | 9/1990 |
| WO | WO 91/06334 A1 | 5/1991 |
| WO | WO 92/04065 A1 | 3/1992 |
| WO | WO 92/07600 A1 | 5/1992 |
| WO | WO 92/09324 A1 | 6/1992 |
| WO | WO 92/15353 A2 | 9/1992 |
| WO | WO 92/17231 A1 | 10/1992 |
| WO | WO 93/24167 A1 | 12/1993 |
| WO | WO 94/11272 A1 | 5/1994 |
| WO | WO 94/14492 A2 | 7/1994 |
| WO | WO 95/34874 A1 | 12/1995 |
| WO | WO 96/16686 A1 | 6/1996 |
| WO | WO 96/16687 A1 | 6/1996 |
| WO | WO 96/39337 A1 | 12/1996 |
| WO | WO 97/12638 A1 | 4/1997 |
| WO | WO 98/01822 A1 | 1/1998 |
| WO | WO 98/56444 A1 | 12/1998 |
| WO | WO 98/56445 A1 | 12/1998 |
| WO | WO 99/36115 A2 | 7/1999 |
| WO | WO 99/57019 A2 | 11/1999 |
| WO | WO 00/09187 A1 | 2/2000 |
| WO | WO 00/59806 A1 | 10/2000 |
| WO | WO 01/28887 A1 | 4/2001 |
| WO | WO 01/29765 A1 | 4/2001 |
| WO | WO 01/37909 A1 | 5/2001 |
| WO | WO 02/072183 A1 | 9/2002 |
| WO | WO 03/101514 A1 | 12/2003 |
| WO | WO 03/103759 A1 | 12/2003 |
| WO | WO 2004/089451 A1 | 10/2004 |
| WO | WO 2006/110080 A1 | 10/2006 |

OTHER PUBLICATIONS

Office Action from counterpart Japanese Application No. 2008-189362, dated Jun. 14, 2011, 4 pages (with translation).

Extended European Search Report for European Application No. 09173845.0, dated Jun. 25, 2010, 18 pages.

Spirale DDS Product Information sheet, Armstrong Medical, [online] [retrieved from internet: URL http://www.amsorbplus.com/products/spirale/spirale-main.htm], [retrieved on Oct. 21, 2009], 1 page.

Office Action from co-pending U.S. Appl. No. 12/603,700, dated Nov. 23, 2012, 17 pages.

* cited by examiner

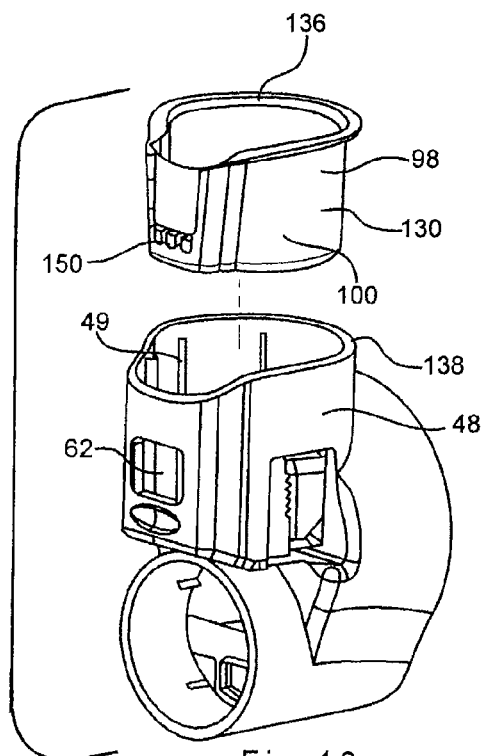
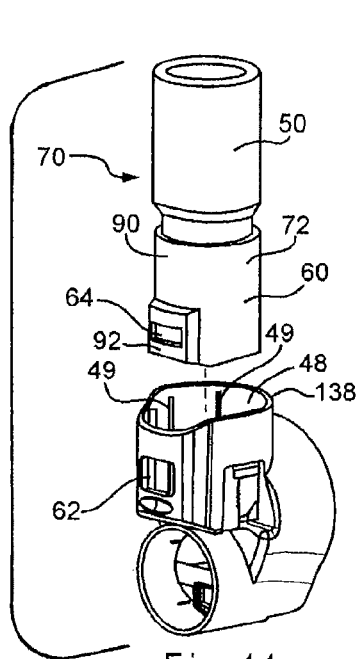 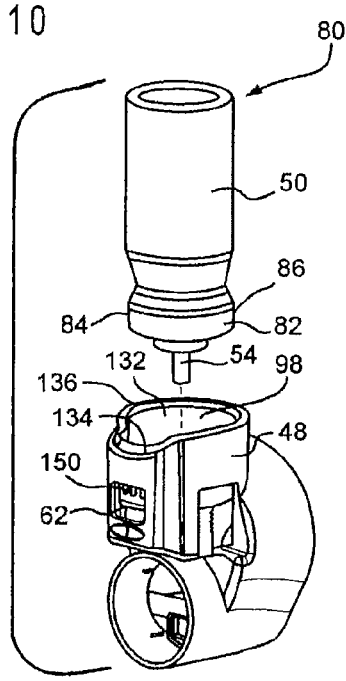
Fig.10
Fig.11
Fig.12

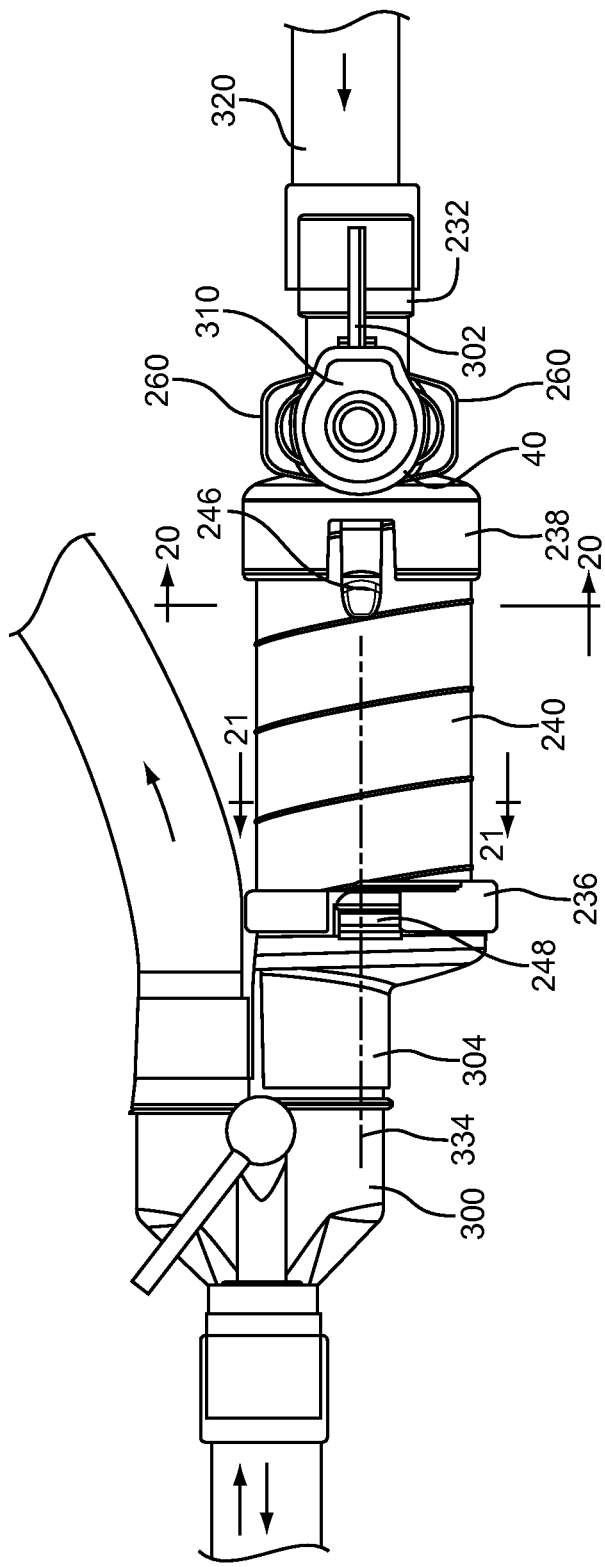

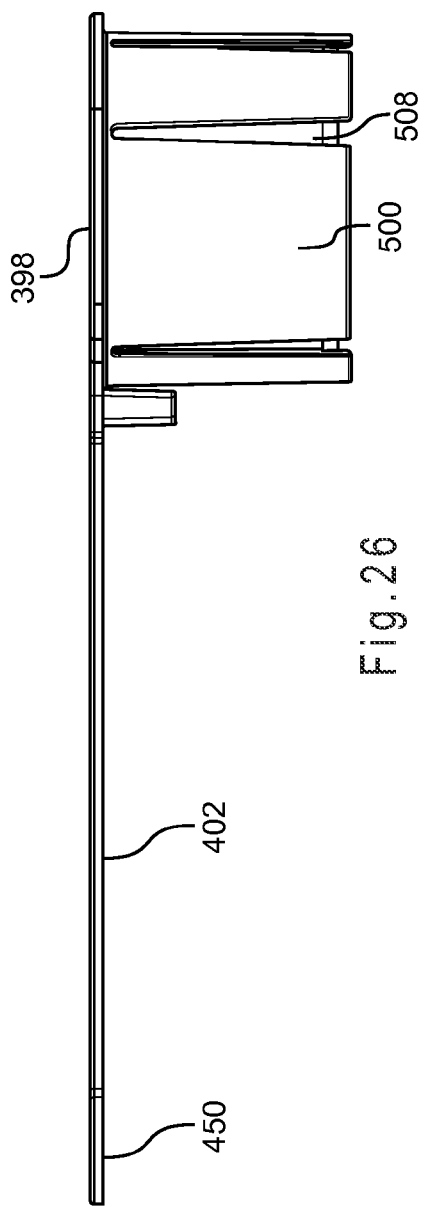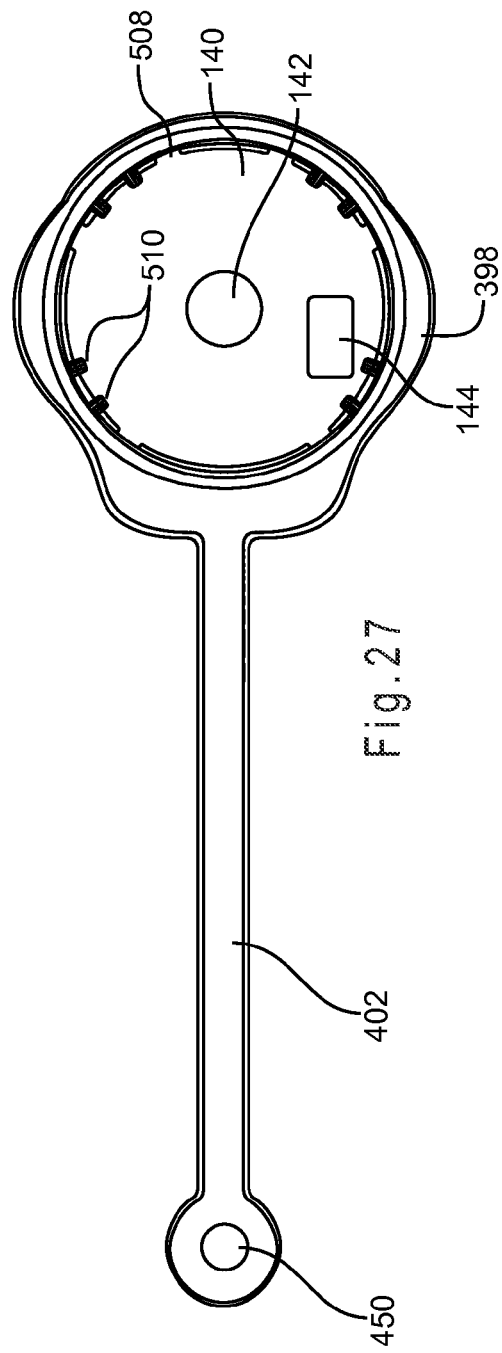

MODULAR AEROSOL DELIVERY SYSTEM

This application is a continuation of U.S. application Ser. No. 12/603,700, filed Oct. 22, 2009, which application claims the benefit of U.S. Provisional Application Ser. No. 61/107,435, filed Oct. 22, 2008, the entire disclosures of which are hereby incorporated herein by reference.

BACKGROUND

The present invention relates generally to an aerosol delivery system, and in particular to a modular aerosol delivery system configured to adapt and support medicament container assemblies having different configurations.

Pressurized Metered Dose Inhalers (PMDI's) are an important delivery mechanism for various medicaments. For example, patients have certain conditions that can be treated with medicaments dispersed in an aerosol and administered to the patient by inhalation. In one format, the aerosol with medicaments is maintained under pressure in a container, and is dispensed in metered, or measured, dosages with an inhalation device, such as an actuator boot. In other arrangements and configurations, the aerosol with medicaments is administered by way of a holding chamber, which can be further incorporated into a ventilator system.

In some circumstances, it can be important for the patient or caregiver to be able to ascertain the number of metered doses remaining in the container, either by an indication of the number remaining therein or by knowledge of the number already dispensed therefrom, such that the patient or caregiver is not caught unaware with an empty container when in need of the medicament. As a result, it is known to secure various indicating devices to the container and/or to the dispenser housing interfacing with the canister. The indicating devices are configured to count and display indicia informing the patient or caregiver about the number of doses used or remaining in the container.

In one example of such a device, as shown for example and without limitation in U.S. Pat. No. 6,431,168, the dose indicator is secured to the container. As such, the corresponding dispenser housing must be shaped to receive a container assembly, which includes the container and dose counter secured thereto. One problem with such a configuration, however, is that the dispenser housing may not be suitably shaped and/or configured to receive and properly actuate a different container assembly, for example a container having a different medication, and which may or may not be equipped with a dose counter or a differently shaped dose counter. This can be particularly troublesome, for example, where the dispenser housing is incorporated into a ventilator circuit and cannot be easily removed therefrom. As such, it may be difficult to administer different types of medication through the same dispenser housing, but instead requires the caregiver to disassemble and reconfigure the ventilator circuit for each type of medication.

For at least these reasons, an improved medication delivery assembly, which can accommodate and actuate different medicament container assemblies, is desirable.

SUMMARY

In a first aspect of the invention, a kit for assembling a medication delivery device includes a dispenser housing having a support block with a well and an orifice communicating with the well. The dispenser housing includes a peripheral wall defining a cavity. A first container assembly includes a valve stem shaped to be received by the well in the support block. The first container assembly has a first exterior shape and is reciprocally moveable along a longitudinal axis defined by the valve stem. The first exterior shape is shaped to be received in the cavity. A second container assembly includes a valve stem shaped to be received by the well in the support block. The second container assembly has a second exterior shape and is reciprocally moveable along a longitudinal axis defined by the valve stem. The second exterior shape is different than the first exterior shape. An insert member is adapted for mounting to the dispenser housing in the cavity and defines an interior space shaped to receive the second exterior shape of the second container. Both the first container assembly and the second container assembly, the latter in combination with the insert member, are adapted to be mounted in the dispenser housing. The first container assembly in combination with the insert member is not adapted to be mounted in the dispenser housing.

In another aspect, a medication delivery device includes a dispenser housing having a support block with a well and an orifice communicating with the well. The dispenser housing includes a first peripheral wall defining a cavity. An insert member is disposed in the cavity of the dispenser housing. The insert member has a second peripheral wall nesting with the first peripheral wall, and a floor defining an interior space. The floor has an opening aligned with the well of the dispenser housing. A medicament container includes a canister and a valve stem, which extends through the opening in the floor and is received in the well in the support block. The canister is reciprocally moveable relative to the valve stem along a longitudinal axis defined by the valve stem.

In yet another aspect, a method for assembling a medication delivery device includes providing first and second identical dispenser housings each having a support block with a well and an orifice communicating with the well. Each of the dispenser housings has a peripheral wall defining a cavity. The method further includes providing a first container assembly having a valve stem shaped to be received by the well in the support block of the first dispenser housing. The first container assembly has a first exterior shape shaped to be received in the cavity of the first dispenser housing, and includes a dose counter. The method further includes inserting the first container assembly in the cavity of the first dispenser housing and disposing the valve stem in the support block of the first dispenser housing. The method also includes providing a second container assembly having a valve stem shaped to be received by the well in the support block of the second dispenser housing. The second container assembly has a second exterior shape different than the first exterior shape. The method further includes disposing an insert member in the cavity of the second dispenser housing. The insert member includes an interior space shaped to receive the second exterior shape of the second container. The method further includes inserting the second container assembly in the interior space of the insert member and disposing the valve stem of the second container assembly in the support block of the second dispenser housing.

In yet another aspect, a ventilator system includes a dispenser housing in fluid communication with an oxygen intake line and a patient interface. The dispenser housing includes a support block having a well and an orifice communicating with the well. The dispenser housing has a peripheral wall defining a cavity. An insert member is adapted for mounting to the dispenser housing in the cavity and defines an interior space. The insert member has a floor with an opening adapted to be aligned with the well of the dispenser housing when the insert member is mounted to the dispenser housing.

In yet another aspect, a method for assembling a medication delivery device includes providing a dispenser housing having a support block with a well and an orifice communicating with the well. The dispenser housing includes a peripheral wall defining a cavity. A first container assembly is inserted in the cavity of the dispenser housing. The method includes removing the first container assembly from the cavity of the dispenser housing, disposing an insert member in the cavity of the dispenser housing, and inserting a second container assembly in the insert member.

In yet another aspect, a medication delivery device includes a first end piece having an input port and a first quick release connector component and a second end piece having an exit port and a second quick release connector component. The first and second quick release connector components are releasably engageable with the first and second end pieces defining an interior space therebetween. A collapsible chamber has opposite ends connected to the first and second end pieces. The collapsible chamber is moveable between a collapsed position and an extended position, wherein an entirety of the collapsible chamber is received in the interior space defined by the first and second pieces when in the collapsed position.

The various aspects and embodiments of the present invention provide significant advantages relative to the prior known devices. In particular, a single dispenser housing can be used to accommodate differently shaped and configured medicament container assemblies. As such, there is no need to manufacture and inventory multiple, complicated and expensive dispenser housings. Instead, a simple and inexpensive insert member can be used to reconfigure the dispenser housing. In addition, this allows the user, such as the caregiver, to use the same dispenser housing to dispense different types of medication, or medications coming in different types of containers. This can be important, for example and without limitation, when the dispenser housing is difficult to remove from a delivery system such as a ventilator system. The collapsible chamber permits the chamber to be collapsed, so as to minimize the size of the device while protecting the chamber from tampering or other damage.

BRIEF DESCRIPTION OF THE DRAWINGS

FIG. 10 is an exploded perspective view of an insert member and a portion of a dispenser housing.

FIG. 11 is an exploded perspective view of a first container assembly and dispenser housing.

FIG. 12 is an exploded perspective view of a second container assembly and a dispenser housing configured with an insert member.

FIG. 19 is view of a medication delivery device incorporated into a ventilator circuit.

FIG. 26 is a side view of an insert member.

FIG. 27 is a top view of an insert member.

DETAILED DESCRIPTION OF THE DRAWINGS

The present disclosure is directed to medication delivery devices, including ventilator circuit aerosol delivery systems. The disclosed ventilator circuit aerosol delivery systems include implementations to be used with intermittent flow ventilators and implementations to be used with continuous flow ventilators. As described in more detail below, by implementing systems to separate an inspired gas flow from an expired gas flow at the entrance to an endotracheal tube, or a tracheotomy tube, and integrating a Wye connector into an MDI ventilator assembly, the MDI ventilator assembly may be moved from the inspired limb and connected directly to the endotracheal tube, or a tracheotomy tube. By connecting the MDI ventilator assembly directly to the endotracheal tube, or tracheotomy tube, aerosolized drugs may be more effectively administered to a patient without "dead space area" where gases exhaled from a patient remain between each breath such that the same gases are inhaled by the patient upon their next breath. Various delivery systems are disclosed for example and without limitation in U.S. Publication No. US 2005-39746A1, entitled Ventilator Circuit and Method for the User Thereof and filed Feb. 9, 2004, U.S. Publication No. US 2006-0254579A1, entitled Ventilator Circuit and Method for the Use Thereof and filed Apr. 24, 2006, and U.S. application Ser. No. 12/105,881, entitled Aerosol Delivery System and filed Apr. 18, 2008, the entire disclosures of which are hereby incorporated herein by reference.

Figure 1:
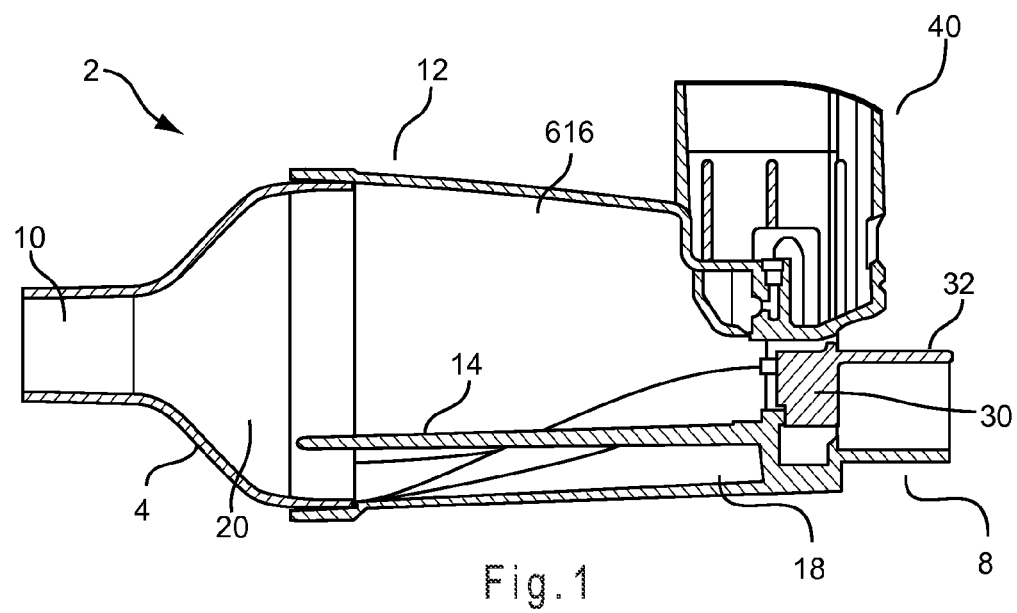
FIG. 1 is a cross-sectional, side view of a first embodiment of a dispenser housing including a holding chamber.
Figure 15:
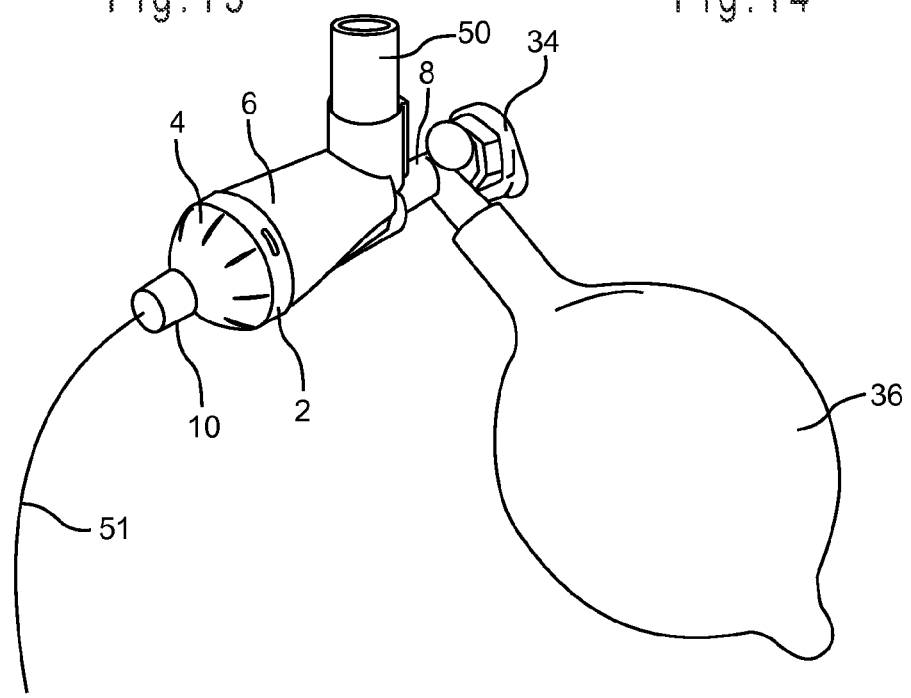
FIG. 15 is a perspective view of a medication delivery device including a resuscitation bag.
Figure 16:
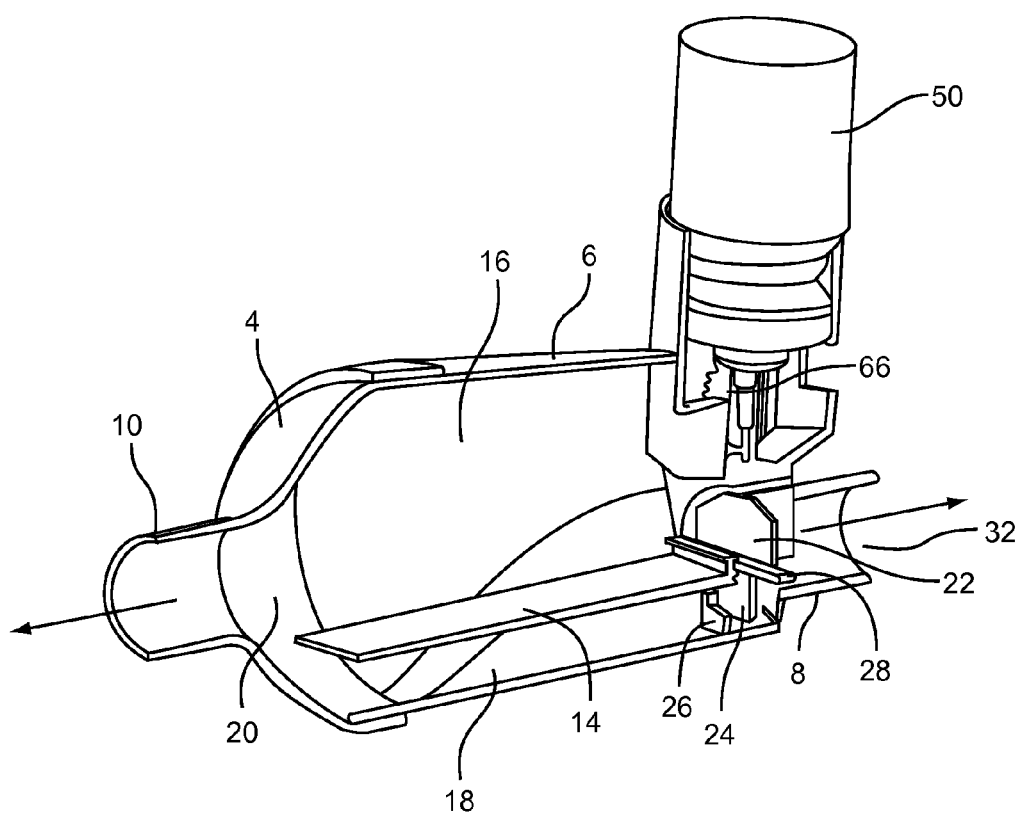
FIG. 16 is a partial, perspective view of a medication delivery device shown in FIG. 15.

Now referring to the embodiment of FIGS. 1, 15 and 16, a dispenser housing 2 includes three primary components. A housing component 4 includes a patient port 10. It should be understood that the housing component 4 can be configured with different patient ports to accommodate various patient interface components, including for example and without limitation endotracheal (ET) tubes, masks, mouthpieces, etc. A second housing component 6 includes an exterior wall 12 and an interior wall 14, or shelf, which separates the chamber into the inhalation and exhalation interior spaces 16, 18. In one embodiment, the spaces 16, 18 communicate with each other at a vestibule area 20 formed in front of and communicating with the patient port. A receptacle 40 is formed on the housing and includes a support block 42 having a well 44 with an orifice 46 that communicates directly with the inhalation interior space 16, as shown in FIGS. 3-10.

Referring again to FIGS. 1, 15 and 16, a third housing component 8 is formed as a connector and defines a ventilator port 32. The connector has first and second passageways separated by a wall, with the first and second passageways communicating with inhalation and exhalation interior spaces 16, 18. Additional walls 30 form a valve seat for the inhalation valve 22. The first and third components 4, 8 are secured to respective ends of the second component 6 to form the dispenser housing. An integrally formed inhalation/exhalation valve 22, 24 is disposed between the connector 8 and the second component 6. The second component 6 has a valve seat 26 for the exhalation valve 24. The valve includes a base portion 28, and inhalation/exhalation flaps 22, 24 extending in opposite directions from the base portion 28. The inhalation valve 22 moves off of the first seat 30 of the connector 8 during inhalation, while the exhalation valve 24 moves off of the second seat 26 during exhalation. In one embodiment, the surface area of the inhalation valve 22 is greater than the surface area of the exhalation valve 24, although it should be understood that the surface areas can be the same, or that the surface area of the inhalation valve is less than the area of the exhalation valve. It should be understood that the inhalation and exhalation valves 22, 24 can be formed separately, again with the same or differential surface areas.

Figure 21:
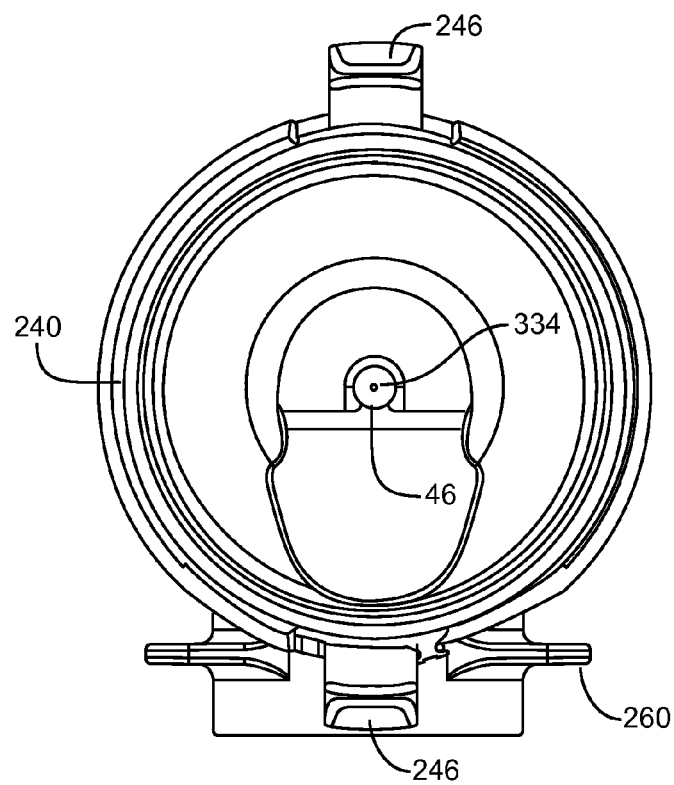
FIG. 21 is a cross-sectional view of the delivery device shown in FIG. 19 taken along line 21-21.
Figure 20:
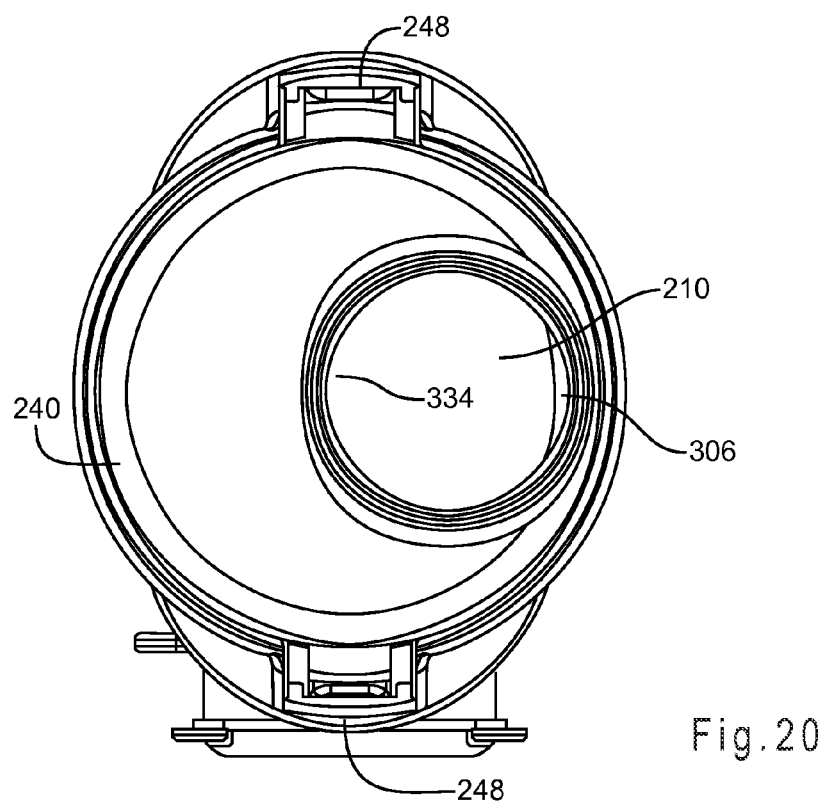
FIG. 20 is a cross-sectional view of the delivery device shown in FIG. 19 taken along line 20-20.
Figure 22:
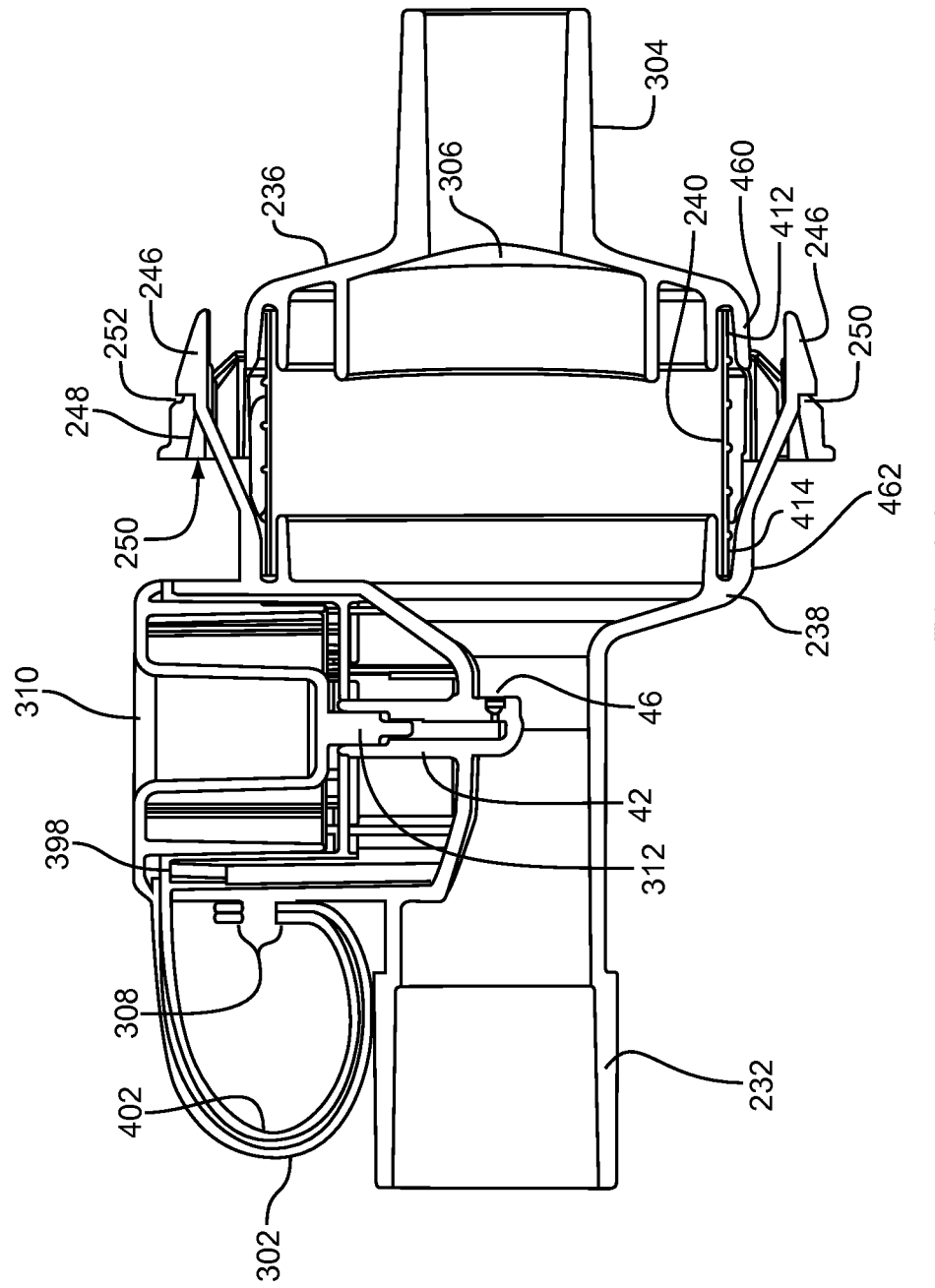
FIG. 22 is a side cross-sectional view of a delivery device shown in a collapsed position.
Figure 23:
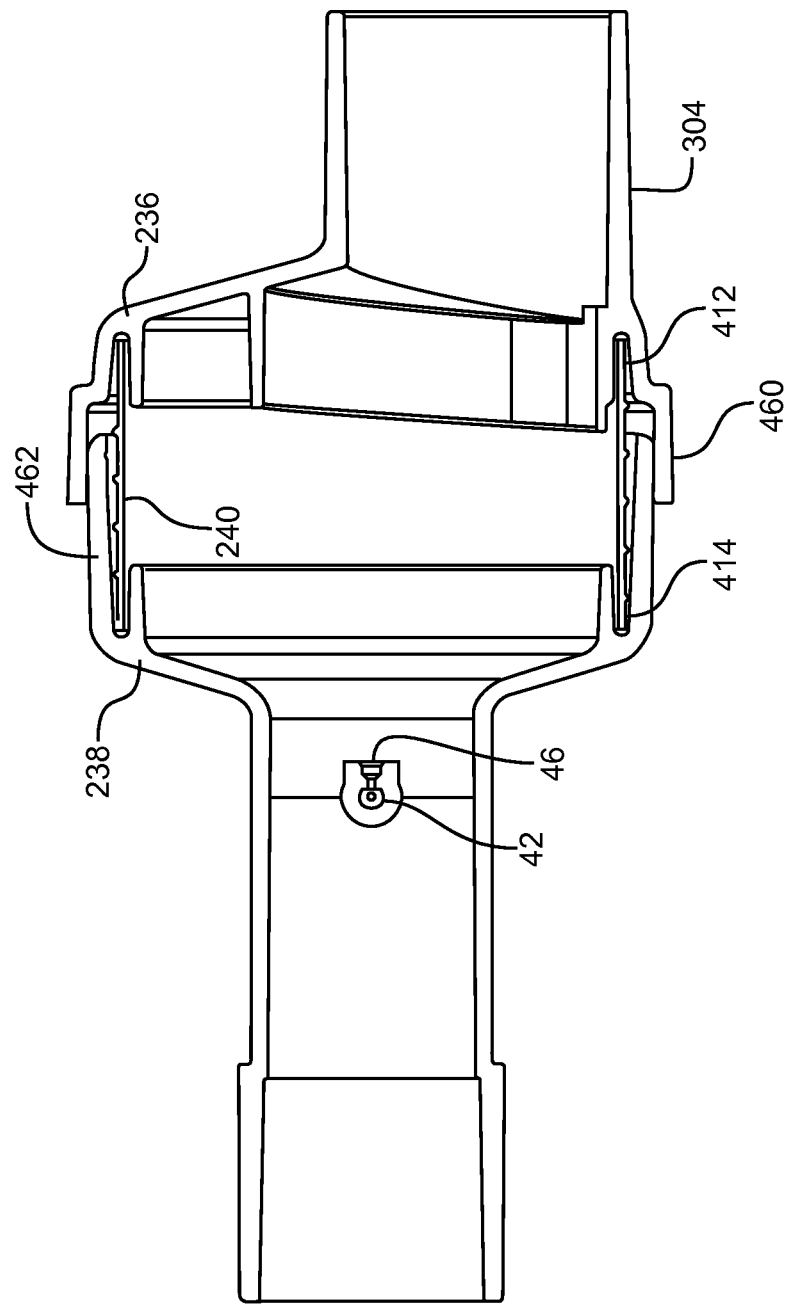
FIG. 23 is a top cross-sectional view of a delivery device shown in a collapsed position.
Figure 24:
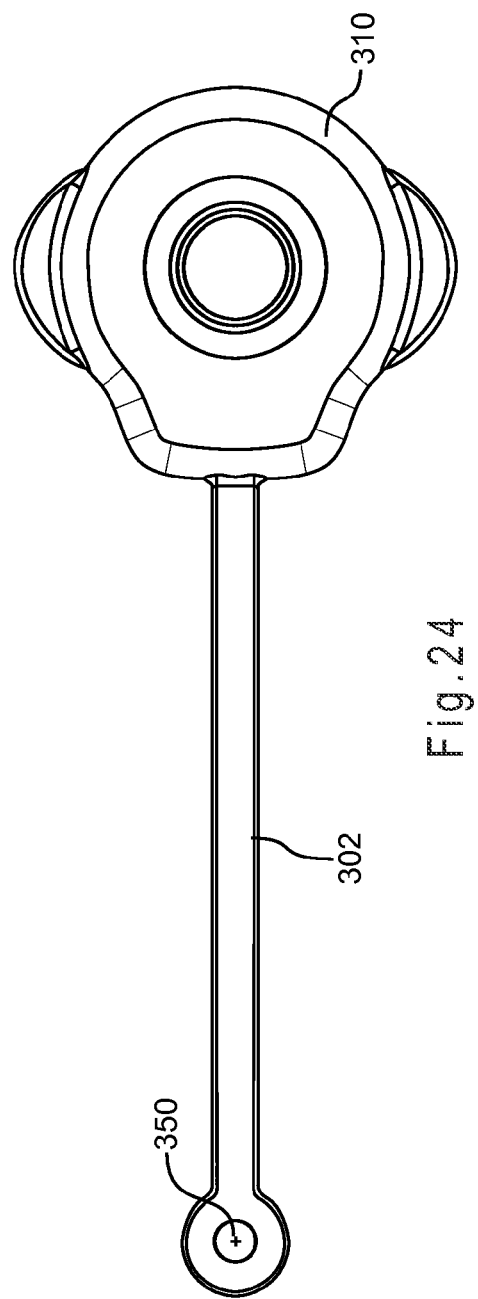
FIG. 24 is a plan view of a plug member.
Figure 25:
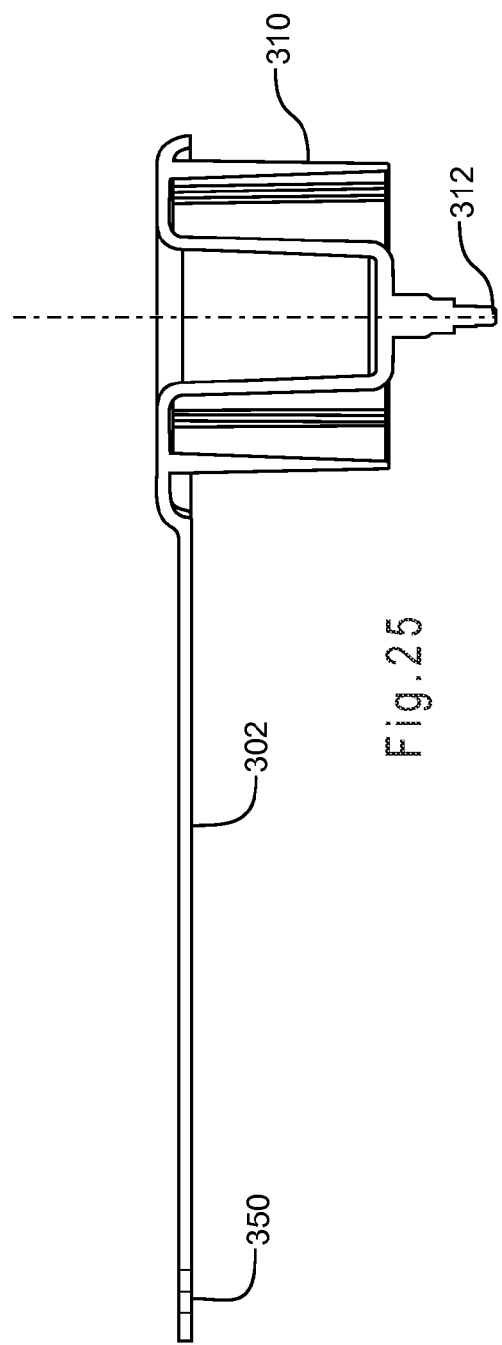
FIG. 25 is a side, cross-sectional view of the plug member shown in FIG. 24.

In operation, the system is pressurized to inflate the lungs of the patient, such as a neonate. The positive pressure comes from an oxygen supply 34 connected to a resuscitation bag 36. Manual resuscitation, for example and without limitation bagging, can begin immediately after birth, for example, to maintain a neonate's breathing. A pressurized metered dose inhaler (pMDI) 50 is actuated or fired in between breaths, with the drug being held in the inhalation interior space 16 of the chamber until the next breath. As the resuscitation bag is squeezed, the flow through the inhalation valve 22 and increase in pressure forces the drug from the inhalation interior space 16 of the chamber through the patient port 10 to the patient, for example through the endotracheal tube 51. As the resuscitation bag 36 reinflates, it creates a negative pressure that pulls air through the exhalation interior space 18 as the exhalation valve 24 is opened, with any drug remaining in the inhalation interior space 16 staying there due to the separation of the inhalation and exhalation interior spaces 16, 18. The next breath forces the remaining drug through the patient port 10 to the patient through the patient interface component. The dispenser housing can be used with a flow inflating resuscitation bag, as described hereinabove, or with a self-inflating resuscitation bag. The self-inflating resuscitation bag includes a non-rebreathing valve that prevents the bag from pulling exhaled gases from the patient, and in particular from the chamber. Instead, the patient exhales into the device and the expiratory gases exit to the atmosphere through the non-breathing valve. With this device, the dispenser housing still separates the exhaled gases because a pressure differential is maintained with a higher pressure at the patient end of the device.

While the embodiments of FIGS. 1, 15 and 16 may still be used with a Wye connector, it should be understood that because inspired gas flow and expired gas flow are separated at the entrance to the endotracheal breathing tube, or tracheotomy tube, the MDI ventilator assembly may be moved from the inspired limb and connected directly to the endotracheal breathing tube or tracheotomy tube.

The disclosed ventilator circuit aerosol delivery system is suitable for use with intermittent flow ventilators and continuous flow ventilators, and including without limitation both mechanical and manual ventilators such as resuscitation bags. As used herein throughout, the term "including" does not means limited to, but rather is without limitation Implementations of the disclosed ventilator circuit aerosol delivery systems provide the ability to connect the MDI ventilator assembly directly to the endotracheal tube, or a tracheotomy tube, due to an integrated Wye connector or the ability to separate inhalation flow and exhalation flow at the entrance to an endotracheal breathing tube or a tracheotomy tube. Connecting the MDI ventilator assemblies directly to the endotracheal tube, or tracheotomy tube, provides the ability to more efficiently administer aerosolized drugs to a patient without "dead space area" where gases exhaled from a patient remain between each breath such that the same gases are inhaled by the patient upon their next breath. For this reason, the MDI ventilator assembly may be left in a ventilator circuit even when the MDI ventilator assembly is not being used to administer an aerosolized drug to a patient so that it is no longer necessary to break a ventilator circuit each time an aerosolized drug is administered to a patient.

Preferably, the housing 2, or it various components 4, 6, 8 individually or in combination, are made of a clear plastic, although it can be non-transparent in certain embodiments. In one implementation, the housing 2, or its various components individually or in combination, may be made from an anti-static material such that a surface resistivity of the housing 2 is less than about 10E12 ohm/sq., and preferably between about 10E10 and about 10E12 ohm/sq. Examples of antistatic housings are disclosed in U.S. patent application Ser. No. 10/821,260, filed Apr. 8, 2004, the entirety of which is hereby incorporated by reference. Further examples of housings used in MDI ventilator assemblies are disclosed in U.S. patent application Ser. No. 10/774,751, filed Feb. 9, 2004 and published as U.S. Publication No. US 2005-39746A1 (entitled Ventilator Circuit and Method for the User Thereof), and U.S. patent application Ser. No. 11/410,270, filed Apr. 24, 2006 U.S. and published as U.S. Publication No. US 2006-0254479A1 (entitled Ventilator Circuit and Method for the User Thereof), the entire disclosures of which are hereby incorporated herein by reference.

It should be appreciated that the housing 2 may additionally define a temperature probe port, a pressure port, and a holder. In one implementation, both the temperature probe port and the pressure port are positioned on the inhalation port. However, in other implementations, one or both of the temperature probe port and the pressure port may be positioned on other portions of the housing such as the exhalation port. It should be understood that the ports, including without limitation the temperature and pressure ports, can be used to monitor other parameters, such as the presence of $CO_2$ or other gases.

Referring to FIGS. 17-23, another embodiment of a medication delivery device includes a housing 202 having a port 232 and a patient port 210, 304. The port 232 can be configured as a ventilator port as described above with respect to the first embodiment. Indeed, as shown in the embodiment of FIG. 19, a WYE-connector 300 is connected to the patient port 304, with a ventilator supply conduit 320 connected to the port 232. As shown in FIGS. 19, 21 and 23, in one embodiment, the patient port 304 is offset from a central, longitudinal axis 334 defined by the chamber, while the orifice 46 is in line with the longitudinal axis 334. A receptacle 40 is configured on a conduit 234 communicating between the port and the housing. The housing includes first and second end pieces 236, 238, with the first end piece including the patient port 210, 304. As shown in FIGS. 21-23, the patient port 304 includes a curved portion 306. A collapsible chamber 240 is disposed between and coupled to the end pieces. U.S. Pat. No. 4,938,210, which is hereby incorporated herein by reference, discloses one embodiment of a collapsible chamber. The chamber defines an interior space. When extended, the chamber has a volume of less than about 150 cc in one embodiment, less than about 130 cc in another embodiment, and less than about 125 cc in another embodiment. The chamber is expandable between a collapsed, stored position (FIGS. 22 and 23) and an extended, use position (FIGS. 17-21). In the stored position, the chamber is collapsed and disposed in spaces 242, and in particular annular grooves 412, 414, formed by the end pieces, which are coupled for example with a quick-release mechanism 244 that can be snapped together. In the stored position, the collapsible chamber is protected from tampering, with the size of the overall device being reduced. In one embodiment, the quick release mechanism includes first and second connector components, which may be interchanged on the first and second end pieces. In one embodiment, the quick release mechanism includes a pair of tabs 246 releasably engaging a corresponding pair of receivers 248 configured with abutment surfaces 252. The tabs are depressed, inserted through openings 250 in the receivers and then released to engage the surfaces. The tabs include grippable portions 254 allowing them to be engaged by the user and thereafter deflected for engagement/insertion and disengagement/withdrawal with the receivers. In the collapsed position, an entirety of the collapsible chamber is received in the interior space 242, 412, 414 defined by the first and second pieces. In one embodiment, each of the first and second end pieces include an annular wall 460, 462 defining the interior space 242, 412, 414, with the annular walls 460, 462 overlapping when the collapsible chamber is moved to the collapsed position as shown in FIGS. 22 and 23. The discharge orifice 46 is in fluid communication with the interior of the collapsible chamber.

Figure 17:
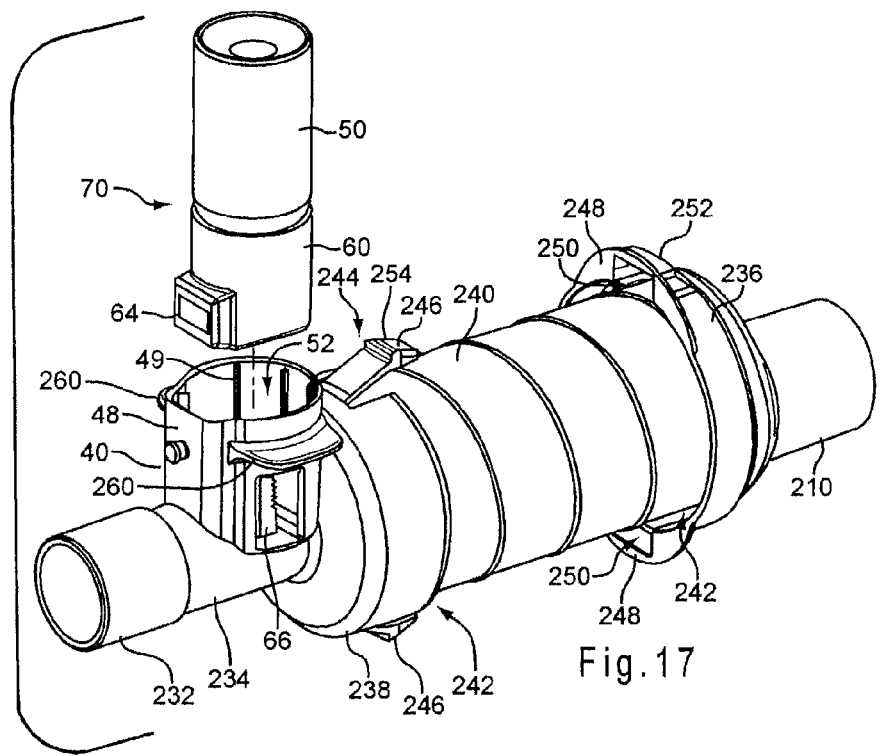
FIG. 17 is a partially exploded perspective view of an alternative embodiment of a medication delivery device.
Figure 18:
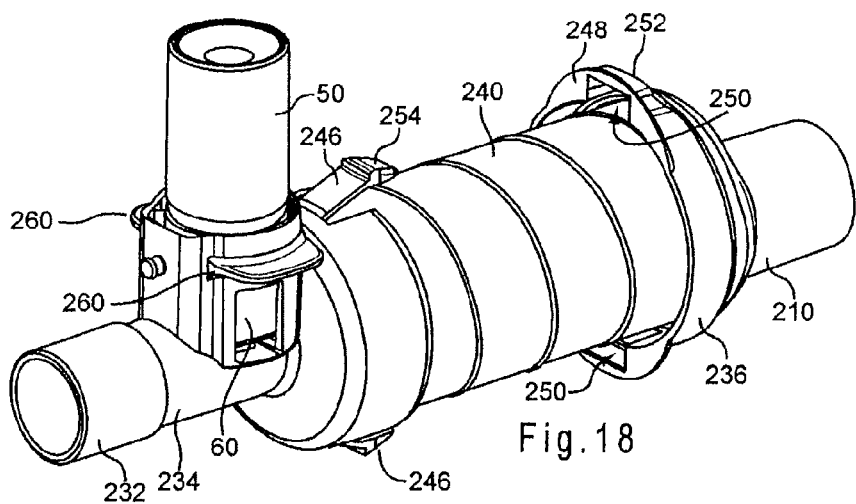
FIG. 18 is an assembled perspective view of the medication delivery device shown in FIG. 17.

Referring to FIGS. 1, 3-6, 10, 15 and 16, the MDI receptacle 40 is typically located on a top of the housing 2, but the MDI receptacle 40 may be located at other positions on the housing 2, for example on the conduit as shown in FIGS. 17 and 18. FIGS. 3-6 and 10-14 presently show only the downstream portion of the housing component 6, and it should be understood that this portion can be made separately or integrally with the remaining portions of housing component 6, or components 4 and 8. The MDI receptacle 40 is positioned away from the patient port 10 such that when an aerosolized drug is dispensed into the interior space 16 via the MDI receptacle 40, the aerosolized drug may expand before being inhaled by a patient via the patient port 10. In particular, it will be appreciated that during inhalation, when gases flow from the interior space 16 to the endotracheal breathing tube, or tracheotomy tube, the aerosolized drug expands and flows to the patient. If any portion of the aerosolized drug is not inhaled during an initial breath, the remaining aerosolized drug is inhaled during subsequent breaths.

Referring to FIGS. 3-6, 10-14 and 17, the MDI receptacle 40 includes a peripheral wall 48 that defines a socket or recess 52 to receive an end of a MDI container 122 such that when the MDI container 50 is placed in the MDI receptacle 40, an actuator nozzle 42 or support block in the recess of the MDI receptacle 40 engages a stem 54 extending from the MDI container 50 and causes the aerosolized drug within the MDI container 50 to be dispensed into the interior space 16 of the housing 2. A plurality of longitudinal ribs 49 are formed along the interior surface of the wall 48. In particular, the stem 52 is received in the well 44 formed in the actuator nozzle or support block 42. The well 44 communicates with the discharge orifice 46, which opens into the interior space 16. It should be understood that the receptacle can be configured to connect to and support medication containers, aerosol dispersal devices, or systems other than the disclosed MDI container 50.

Figure 2:
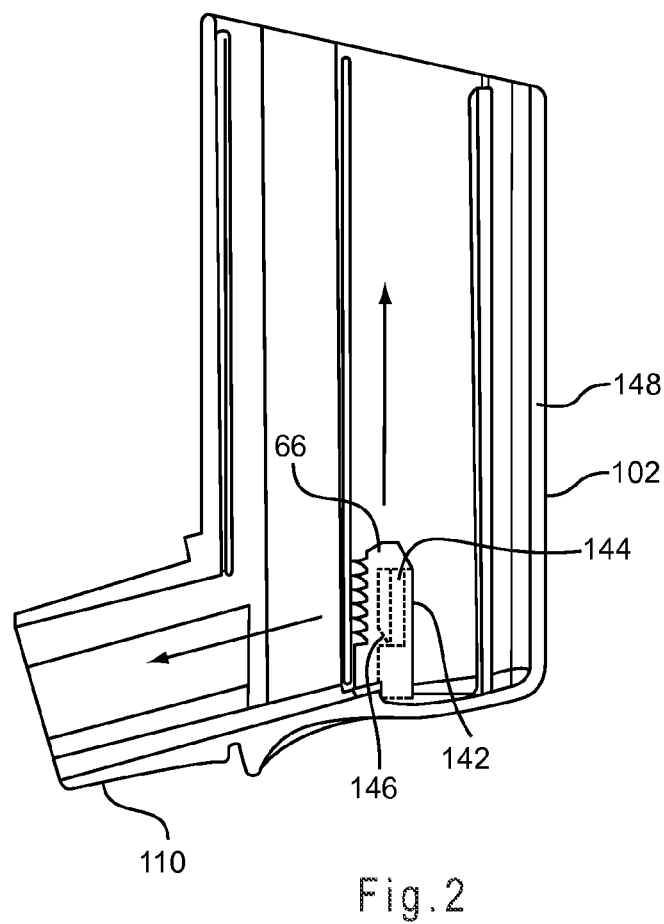
FIG. 2 is a cross-sectional, side view of a second embodiment of a dispenser housing.
Figure 3:
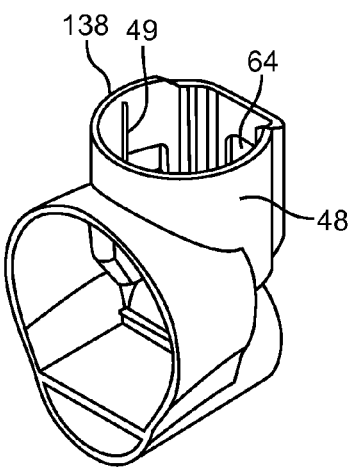
FIG. 3 is a perspective view of a portion of the dispenser housing shown in FIG. 1.
Figure 4:
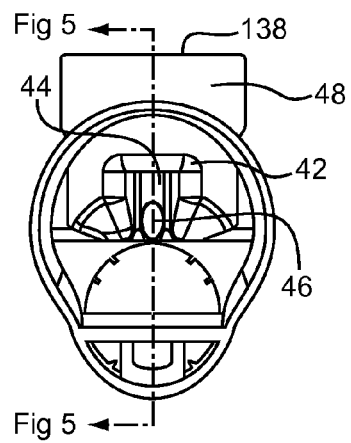
FIG. 4 is a front view of the dispenser housing portion shown in FIG. 3.
Figure 5:
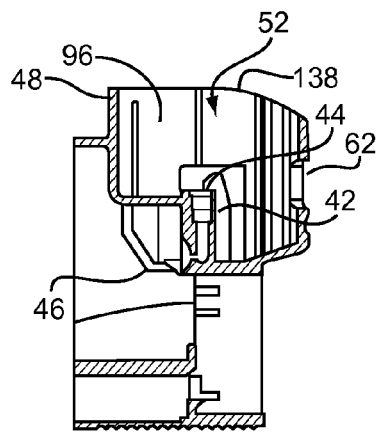
FIG. 5 is a cross-sectional side view of the dispenser housing portion taken along line 5-5 of FIG. 4.

In an alternative embodiment, shown in FIG. 2, a dispenser housing 102 is formed as an actuator boot, with a mouthpiece 110 and a peripheral wall 148 defining a cavity 152 or interior space. Again, the housing includes a support block 142 configured with a well 144 and discharge orifice 146.

Referring to the embodiment of FIGS. 17 and 18, the receptacle is configured with two laterally extending tabs or wings 260. In this embodiment, the user positions two fingers (e.g., first and second) underneath the wings 260 and actuates the container with a thumb. As such, the fingers and thumb do not have to span as great a distance as the other embodiments, for example engaging the bottom of the housing component 8 opposite the container. The wings may also be incorporated into the other embodiments, including for example and without limitation the embodiment of FIGS. 1 and 2. The wings are sized and shaped to provide sufficient surface area to grip. For example and without limitation, in one embodiment, the wings have a depth of about 6 mm and a width of about 18 mm.

Figure 6:
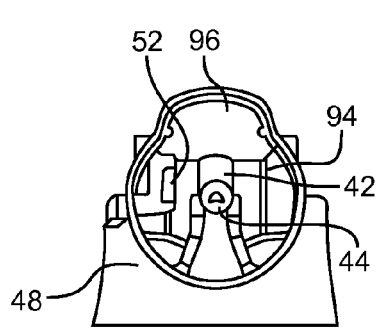
FIG. 6 is a top view of the dispenser housing portion shown in FIG. 3.
Figure 7:
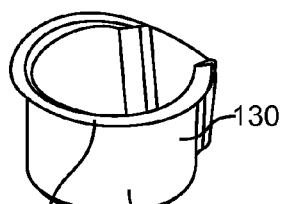
FIG. 7 is a perspective view of an insert member shaped to be received in the dispenser housing shown in FIG. 1.
Figure 8:
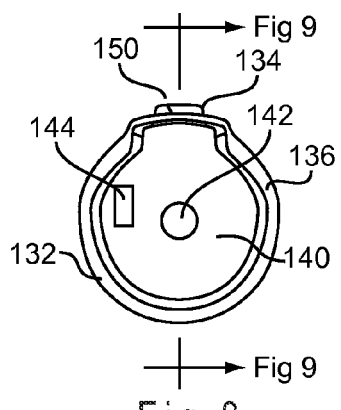
FIG. 8 is a top view of the insert member shown in FIG. 7.
Figure 13:
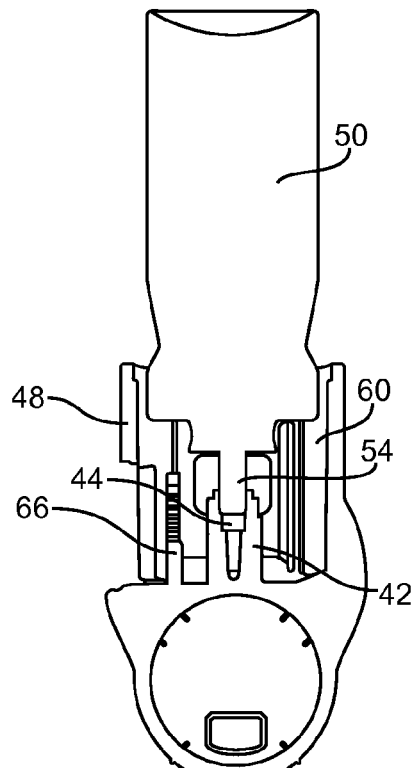
FIG. 13 is a cross-sectional view of the first container assembly and dispenser housing in an assembled configuration.

Referring to FIGS. 11, 13 and 17, a first container assembly 70 includes a dose counter 60 secured to a container 50. The dose counter 60 includes a counting mechanism, mechanical or electrical, including for example and without limitation mechanisms disclosed in U.S. Pat. Nos. 6,997,349 and 6,729,330 (the entire disclosures of which are hereby incorporated herein by reference), with a viewing window 64 displaying various dosage indicia, whether mechanical or electrical/digital. The peripheral wall 48 of the dispenser housing is also configured with a viewing window 62 or opening shaped and positioned to be aligned with the viewing window 64 of the dose counter when the valve stem 54 of the first container assembly is secured in the well 44 of the dispenser housing. Alternatively, the viewing window may be omitted from the dispenser housing as shown in FIGS. 17 and 18, although it should be understood that a viewing window may be incorporated into the embodiment of FIGS. 17 and 18. As shown in FIGS. 2, 13 and 17, an upright member 66 or finger is configured as an actuator. The actuator is positioned such that reciprocal movement of the first container assembly relative to the dispenser housing causes the dose counter to advance and record a dispersement of medication. The first container assembly 70, including the dose counter 60, has a first exterior shape 72 defined by the exterior surface of the dose counter 60, including the viewing window 64. For example, in a cross-section substantially perpendicular to a longitudinal axis defined by the valve stem 54, the cross section substantially mates with the interior space of the socket 52 as shown in FIG. 6, and includes a circular portion 90 and a protuberance 92 extending outwardly from a diameter of the circular portion, thereby forming a "keyhole" shape. The circular portion 90 and protuberance 92 mate with a circular portion 94 of the socket and a recess 96 extending laterally outwardly therefrom respectively.

Figure 14:
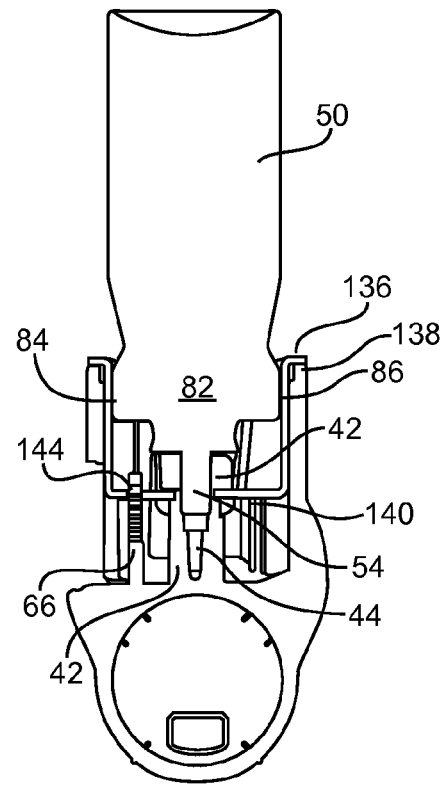
FIG. 14 is a cross-sectional view of the second container assembly and dispenser housing in an assembled configuration.

Referring to FIGS. 12 and 14, a second container assembly 80 is configured as a canister 50 with an end portion 82, including a ferrule, and a valve stem 54 extending therefrom. The second container assembly 80 has a second exterior shape 84 defined by the exterior surface 86 of the end portion of the canister. For example, as shown in FIG. 12, the second exterior shape 84 in cross section is substantially circular defined by the diameter of the end portion. As shown in FIGS. 11 and 12, the second exterior shape 84 of the second container assembly is different than the first exterior shape 72 of the first container assembly. It should be understood that other container assemblies may have further additional, different exterior shapes defined for example and without limitation by differently sized and shaped canisters, e.g., with end portions having different diameters, with or without differently configured and shaped dose counters.

Since the second exterior shape 84 of the second container assembly is different than the first exterior shape 72 of the first container assembly, and in particular has a smaller overall cross-sectional area taken perpendicular to the longitudinal axis defined by the valve stem 54, the second container assembly 80 may feel sloppy relative to the socket 52 when mounted to the support block 42 due to the excess room between the exterior surface of the canister 50, and the end portion in particular, and the interior surface of the peripheral wall 48 of the dispenser housing.

To improve the fit of the second container assembly 84, an insert member 98, 398 is provided, as show in FIGS. 6-10, 12, 14, 22, 26 and 27. The insert member has a peripheral wall 100, 500 that is nested inside the peripheral wall of the dispenser housing and has an exterior shape 130 that mates with the interior profile of the dispenser housing wall. As shown in FIGS. 26 and 27, the wall 500 may include slots 508, as well as ribs 510 that engage the container. In one embodiment, the exterior shape includes a circular portion 132 and a protuberance 134. The insert member further includes an upper peripheral rim 136, 502 that extends outwardly from the peripheral wall and engages a top edge 138 of the dispenser housing wall. The insert member 98, 398 is configured with a floor 140 having an opening 142 aligned with and positioned above the support block and well and shaped to receive the valve stem 54 of the canister. Alternatively, the support block can extend through the floor, as long as the discharge orifice is located beneath the floor and in communication with the holding chamber or mouthpiece. The floor 140 also includes a second opening 144 shaped to receive or accommodate the upright finger 66 or actuator, which may not have any function relative to a second container assembly not configured with a dose counter. The insert member 98, 398 supports the canister 50 during insertion and use, and prevents the valve stem 54 from missing the well 44 during insertion. The floor 140, with its opening 142, further helps locate and align the valve stem 54 with the support block 42 and well 44. In connection with the embodiment of FIG. 2, the insert member may be longer with an upper rim engaging the top of the actuator, or the insert member may not be configured with a peripheral rim.

As shown in FIGS. 19, 22, 26 and 27, the insert member 398 includes a flexible tether 402 having an end portion 450 with an opening that is secured over a button 308 extending from the exterior surface of the receptacle 40. It should be understood that the tether can be integrally formed with the insert member, or can be configured as a separate member, whether formed as a cord, chain, retractable member, or other similar device. In this way, the insert member 398 can be removed, for example when a first container assembly 70 with a dose counter 60 is being used with the dispenser system, but with it remaining connected to the dispenser system with the tether 402 such that it is not lost or otherwise displaced. As shown in FIGS. 19, 22, 24 and 25, a plug member 310, having wings 332 for gripping by the user, can be inserted into the insert member 398 when the system is not in use, or when the insert member is disconnected from the receptacle, so as to prevent contaminants from entering the insert member or receptacle. The plug member 310 includes a tether 302 having an end portion with an opening, which can be secured over the button. It should be understood that the tether can be integrally formed with the insert member, or can be configured as a separate member, whether formed as a cord, chain, retractable member, or other similar device. The plug member 310 includes an orifice insert 312 that is disposed in the well of the support block to plug the well and prevent contamination thereof. The insert 312 extends through the opening 142 in the bottom of the insert member 398.

Figure 9:
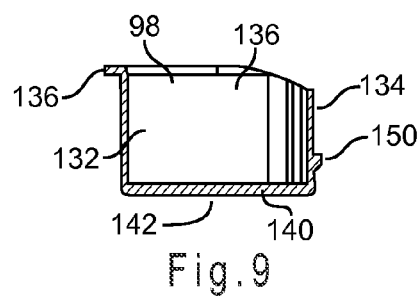
FIG. 9 is a cross-sectional side view of the insert member taken along line 9-9 of FIG. 8.

In operation, the user, such as caregiver, can use different container assemblies 70, 80, having different exterior shapes 72, 84, with the same dispenser housing 2, 102. For example and without limitation, the caregiver can first dispose the first container assembly 70 with dose counter 60 in the dispenser housing 2, 102, and in particular the socket 52, and actuate the first container assembly a predetermined number of times, including for example a single actuation. The dose counter 60 records the predetermined number of actuations. The caregiver can then remove the first container assembly 70 without having to remove the dispenser housing 2, for example, from a ventilator circuit, or alternatively without having locate another actuator 102 for use with another container assembly. Subsequently, for example if a different medication is required, the caregiver can install an insert member 98, 398 into the dispenser housing 2, 102 and then insert a second container assembly 80, for example a canister 50 without a dose counter, into the insert member 98, 398 and engage the support block 42 of the dispenser housing with the valve stem 54 of the canister. The insert member 98 can be installed in the dispenser housing with a snap-fit, a press fit or any other suitable mechanism for securing the insert member. For example, as shown in FIG. 9, one embodiment of the insert member 98 includes a tab 150 that engages the upper edge of the viewing window 62 with a snap fit as shown in FIG. 12. This same operation can be carried out with the actuator boot shown in FIG. 2, with the insert member configured as needed to be fitted in the boot (e.g., without a rim). In this way, it should be understood that the system and method may be incorporated into systems other than ventilator circuits, including the actuator boot of FIG. 2 and/or a spacer configuration.

It is intended that the foregoing detailed description be regarded as illustrative rather than limiting, and that it be understood that it is the following claims, including all equivalents, that are intended to define the spirit and scope of this invention.

The invention claimed is:

1. An adapter for use in a breathing circuit, the adapter comprising:
  a housing comprising a conduit having a ventilator port adapted to be coupled to a breathing circuit and a patient port adapted to communicate with a patient interface, wherein said ventilator port and said patient port are spaced apart in a longitudinal direction, and further comprising a medicament container receptacle communicating with said conduit between said ventilator port and said patient port, said conduit comprising a collapsible chamber defining an interior space, wherein said chamber is expandable between a collapsed position and an extended position, wherein said interior space has a uniform cross section along said longitudinal direction when in said extended position, said receptacle comprising a support block having a well shaped to receive a valve stem extending from a container of medicament and an actuator finger extending upwardly in said receptacle adjacent said support block, wherein said actuator finger is adapted to actuate a dose counter coupled to the container, and wherein said actuator finger is non-moveable relative to said support block, and wherein said housing comprises a first end piece including said patient port and a second end piece including said ventilator port, wherein said collapsible chamber is disposed between said first and second end pieces and wherein said second end piece comprises said medicament container receptacle, said first and second end pieces comprising respectively first and second annular walls, wherein said first and second annular walls are arranged in an overlapping relationship when said chamber is in said collapsed position.

2. The adapter of claim 1 wherein said finger extends parallel to said support block.

3. The adapter of claim 1 wherein said finger comprises a plurality of teeth formed along one side thereof.

4. The adapter of claim 1 further comprising a side wall extending parallel to and surrounding at least a portion of said support block.

5. The adapter of claim 4 wherein said side wall has an opening therein, wherein said finger is visible through said opening.

6. The adapter of claim 1 further comprising an orifice communicating with said well, and wherein said orifice opens directly into said conduit.

7. A medication delivery device comprising:
a housing comprising a conduit having a ventilator port adapted to be coupled to a breathing circuit and a patient port adapted to communicate with a patient interface, wherein said ventilator port and said patient port are spaced apart in a longitudinal direction, and further comprising a medicament container receptacle communicating with said conduit between said ventilator port and said patient port, said conduit comprising a collapsible chamber defining an interior space, wherein said chamber is expandable between a collapsed position and an extended position, wherein said interior space has a uniform cross section along said longitudinal direction when in said extended position, said receptacle comprising a support block having a well and an actuator finger extending upwardly in said receptacle adjacent said support block, and wherein said actuator member is non-moveable relative to said support block, and wherein said housing comprises a first end piece including said patient port and a second end piece including said ventilator port, wherein said collapsible chamber is disposed between said first and second end pieces and wherein said second end piece comprises said medicament container receptacle, said first and second end pieces comprising respectively first and second annular walls, wherein said first and second annular walls are arranged in an overlapping relationship when said chamber is in said collapsed position; and
a medicament container comprising a canister and a valve stem received in said well in said support block, wherein said canister is reciprocally moveable relative to said valve stem along a longitudinal axis defined by said valve stem.

8. The medication delivery device of claim 7 wherein said medicament container is configured with a dose counter, wherein said actuator finger is configured to actuate said dose counter in response to said reciprocal movements of said canister relative to said valve stem.

9. The medication delivery device of claim 7 further comprising an oxygen intake line coupled to said ventilator port.

10. The medication delivery device of claim 7 further comprising an orifice communicating with said well, and wherein said orifice opens directly into said conduit.

11. A kit for assembling a medication delivery device, the kit comprising:
a housing comprising a conduit having a ventilator port adapted to be coupled to a breathing circuit and a patient port adapted to communicate with a patient interface, wherein said ventilator port and said patient port are spaced apart in a longitudinal direction, and further comprising a medicament container receptacle communicating with said conduit between said ventilator port and said patient port, said conduit comprising a collapsible chamber defining an interior space, wherein said chamber is expandable between a collapsed position and an extended position, wherein said interior space has a uniform cross section along said longitudinal direction when in said extended position, said receptacle comprising a support block having a well and an actuator finger extending upwardly in said receptacle adjacent said support block, and wherein said housing comprises a first end piece including said patient port and a second end piece including said ventilator port, wherein said collapsible chamber is disposed between said first and second end pieces and wherein said second end piece comprises said medicament container receptacle, said first and second end pieces comprising respectively first and second annular walls, wherein said first and second annular walls are arranged in an overlapping relationship when said chamber is in said collapsed position;
a first medicament container assembly comprising a valve stem shaped to be received by said well in said support block, said first medicament container assembly configured without a dose counter and being reciprocally moveable along a longitudinal axis defined by said valve stem, wherein said actuator finger does not interfere with said reciprocal movement of said first medicament container assembly; and
a second medicament container assembly comprising a valve stem shaped to be received by said well in said support block, said second medicament container assembly configured with a dose counter and being reciprocally moveable along a longitudinal axis defined by said valve stem, wherein said actuator finger is configured to actuate said dose counter in response to said reciprocal movements of said second medicament container assembly relative to said valve stem.

12. The kit of claim 11 wherein said finger extends parallel to said support block.

13. The kit of claim 11 wherein said finger comprises a plurality of teeth formed along one side thereof.

14. The kit of claim 11 further comprising a side wall extending parallel to and surrounding at least a portion of said support block.

15. The kit of claim 14 wherein said side wall has an opening therein, wherein said finger is visible through said opening.

16. The kit of claim 11 further comprising an orifice communicating with said well, and wherein said orifice opens directly into said conduit.

17. A kit for assembling a medication delivery device, the kit comprising:
a housing comprising a conduit having a ventilator port adapted to be coupled to a breathing circuit and a patient port adapted to communicate with a patient interface, wherein said ventilator port and said patient port are spaced apart in a longitudinal direction, and further comprising a medicament container receptacle communicating with said conduit between said ventilator port and said patient port, said conduit comprising a collapsible chamber defining an interior space, wherein said chamber is expandable between a collapsed position and an extended position, wherein said interior space has a uniform cross section along said longitudinal direction when in said extended position, said receptacle comprising a support block having a well, and wherein said housing comprises a first end piece including said patient port and a second end piece including said ventilator port, wherein said collapsible chamber is disposed between said first and second end pieces and wherein said second end piece comprises said medicament container receptacle, said first and second end pieces comprising respectively first and second annular walls, wherein said first and second annular walls are arranged in an overlapping relationship when said chamber is in said collapsed position;

a first container assembly comprising a valve stem shaped to be received by said well in said support block, said first container assembly having a first exterior shape and being reciprocally moveable along a longitudinal axis defined by said valve stem, wherein said first exterior shape is shaped to be received in said receptacle;

a second container assembly comprising a valve stem shaped to be received by said well in said support block, said second container assembly comprising a dose counter wherein said second container assembly has a second exterior shape and is reciprocally moveable along a longitudinal axis defined by said valve stem, wherein said second exterior shape is different than said first exterior shape, and wherein said dose counter is actuated by said reciprocal movement of said second container assembly; and wherein both of said first container assembly and said second container assembly are adapted to be mounted in said housing.

18. The kit of claim 17 wherein said housing further comprises an actuator finger extending upwardly in said receptacle adjacent said support block, wherein said actuator finger is configured to actuate said dose counter.

19. The kit of claim 18 wherein said finger extends parallel to said support block.

20. The kit of claim 19 wherein said finger comprises a plurality of teeth formed along one side thereof.

* * * * *